United States Patent
Cao et al.

(10) Patent No.: US 11,201,000 B2
(45) Date of Patent: *Dec. 14, 2021

(54) X-RAY IMAGING WITH A DETECTOR CAPABLE OF RESOLVING PHOTON ENERGY

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/891,152

(22) Filed: Jun. 3, 2020

(65) Prior Publication Data

US 2020/0292475 A1  Sep. 17, 2020

Related U.S. Application Data

(63) Continuation of application No. 15/309,328, filed as application No. PCT/CN2015/088220 on Aug. 27, 2015, now Pat. No. 10,705,031.

(51) Int. Cl.
*G21K 7/00* (2006.01)
*A61B 6/00* (2006.01)
*G01N 23/046* (2018.01)
*G01T 1/36* (2006.01)

(52) U.S. Cl.
CPC .............. *G21K 7/00* (2013.01); *A61B 6/4241* (2013.01); *G01N 23/046* (2013.01); *G01N 2223/423* (2013.01); *G01T 1/366* (2013.01)

(58) Field of Classification Search
CPC .................................. G21K 7/00; G01T 1/366
See application file for complete search history.

(56) References Cited

U.S. PATENT DOCUMENTS

| 5,199,057 A * | 3/1993 | Tamura ..................... G21K 7/00 378/43 |
| 9,915,741 B2 * | 3/2018 | Cao ......................... G01T 1/2928 |
| 10,007,007 B2 * | 6/2018 | Cao .................. H01L 27/14634 |
| 10,007,009 B2 * | 6/2018 | Cao .......................... G01T 1/247 |
| 10,061,038 B2 * | 8/2018 | Cao ........................... G01T 1/17 |
| 10,061,040 B2 * | 8/2018 | Cao ........................ G01T 1/2928 |

(Continued)

OTHER PUBLICATIONS

Sun, Tianxi, and C. A. MacDonald. "Full-field transmission x-ray imaging with confocal polycapillary x-ray optics." Journal of applied physics 113.5 (2013): 053104.

*Primary Examiner* — Chih-Cheng Kao
(74) *Attorney, Agent, or Firm* — IPro, PLLC; Qian Gu

(57) ABSTRACT

The present teaching relates to methods, systems, and apparatus for X-ray imaging with a detector capable of resolving photon energy. In one example, an X-ray microscope is disclosed. The X-ray microscope comprises an X-ray source and a detector. The X-ray source is configured for irradiating X-ray to a sample. The detector is configured for: detecting X-ray photons from the irradiated X-ray, determining energy of each of the detected X-ray photons, and generating an image of the sample based on detected X-ray photons that have energies in a predetermined range.

14 Claims, 20 Drawing Sheets

(56) References Cited

U.S. PATENT DOCUMENTS

| | | | |
|---|---|---|---|
| 10,413,264 B2* | 9/2019 | Cao | A61B 6/0435 |
| 10,416,324 B2* | 9/2019 | Cao | H04N 5/3745 |
| 10,502,843 B2* | 12/2019 | Cao | G01T 1/247 |
| 10,514,472 B2* | 12/2019 | Cao | G01T 1/2928 |
| 10,535,703 B2* | 1/2020 | Cao | A61B 6/032 |
| 10,539,691 B2* | 1/2020 | Cao | G01T 1/247 |
| 10,677,940 B2* | 6/2020 | Cao | G01T 1/242 |
| 10,677,941 B2* | 6/2020 | Cao | H01L 31/115 |
| 10,705,031 B2* | 7/2020 | Cao | G01N 23/046 |
| 10,712,456 B2* | 7/2020 | Cao | G01T 1/2928 |
| 10,788,593 B2* | 9/2020 | Cao | G01T 1/242 |
| 10,820,867 B2* | 11/2020 | Cao | G01T 1/2928 |
| 10,820,882 B2* | 11/2020 | Cao | G01T 1/2018 |
| 10,833,217 B2* | 11/2020 | Cao | G01T 1/24 |
| 10,838,086 B2* | 11/2020 | Cao | G01T 1/24 |
| 10,945,688 B2* | 3/2021 | Cao | G01T 1/247 |
| 10,966,676 B2* | 4/2021 | Cao | A61B 6/502 |
| 11,013,479 B2* | 5/2021 | Cao | G01N 23/04 |
| 2005/0168820 A1 | 8/2005 | Yun et al. | |
| 2008/0061234 A1 | 3/2008 | Nakamura | |
| 2008/0260094 A1* | 10/2008 | Carmi | A61B 6/482 378/19 |
| 2010/0020924 A1* | 1/2010 | Steadman Booker | G01T 1/17 378/19 |
| 2014/0072104 A1* | 3/2014 | Jacobsen | G01N 23/04 378/62 |
| 2016/0292891 A1* | 10/2016 | O'Donnell | G06T 11/206 |

* cited by examiner

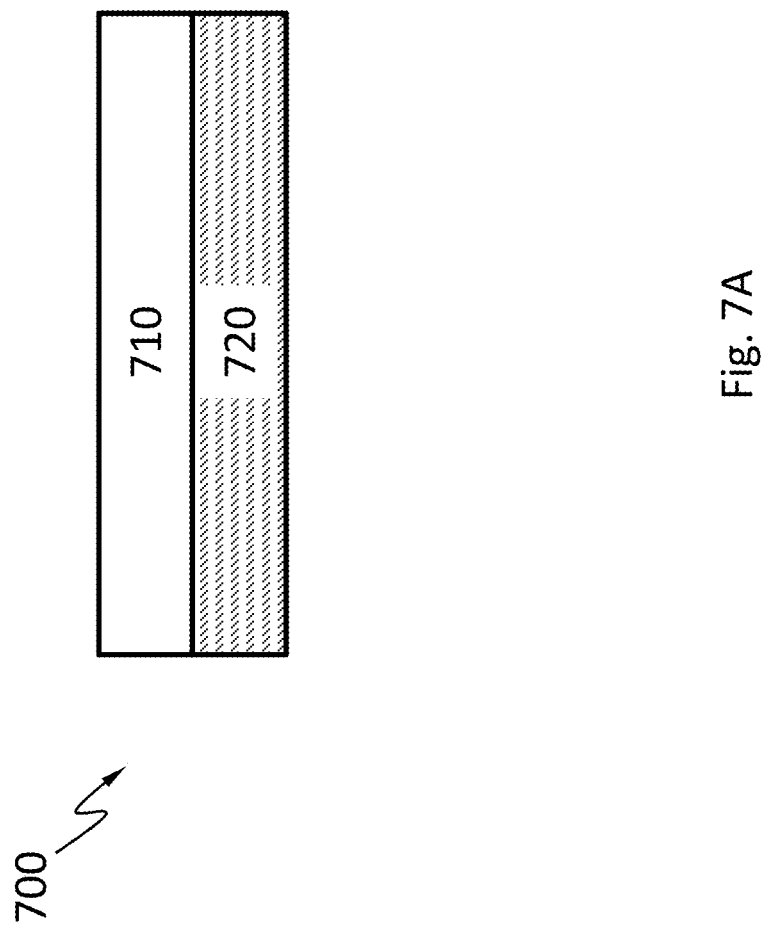

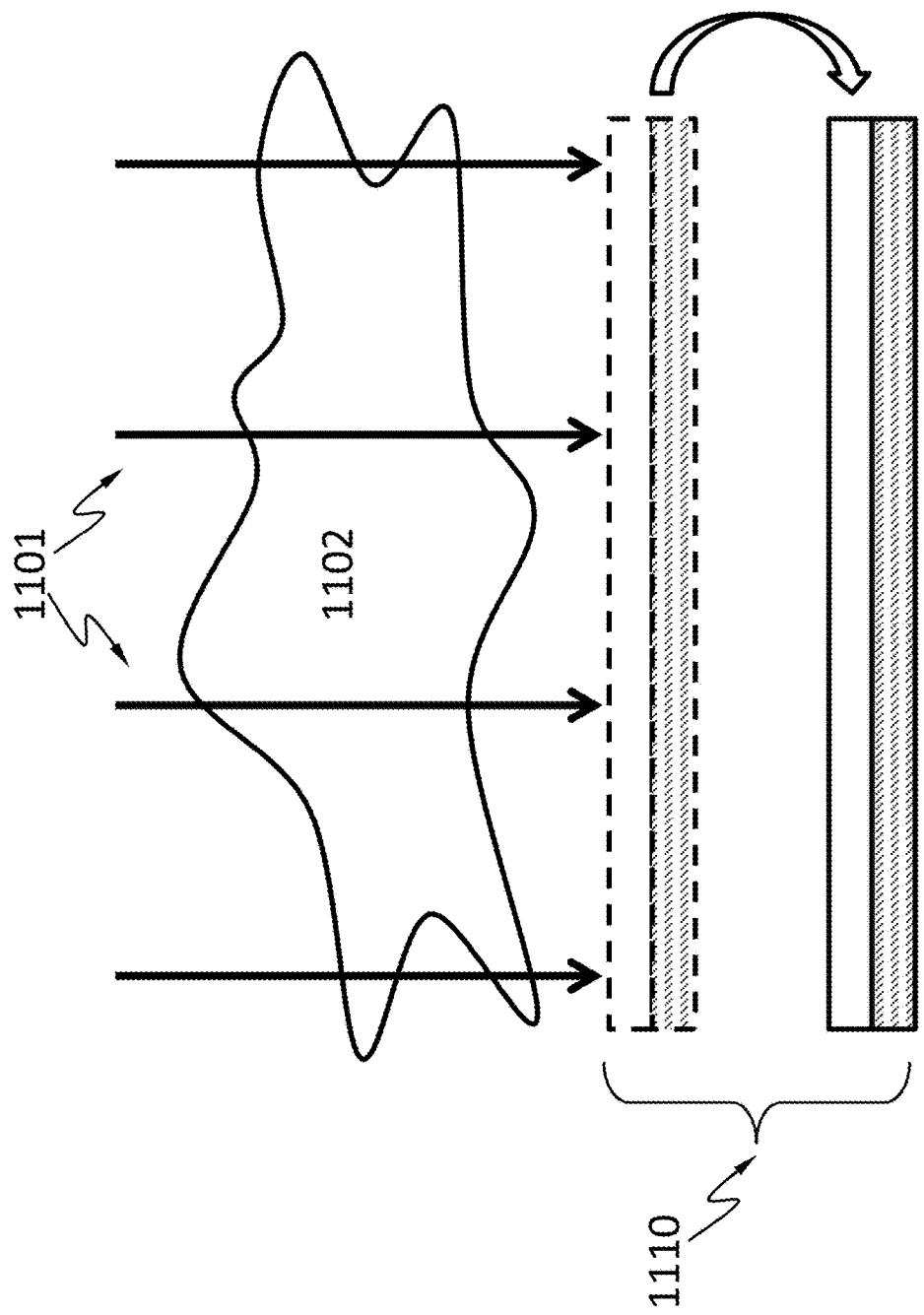

X-RAY IMAGING WITH A DETECTOR CAPABLE OF RESOLVING PHOTON ENERGY

TECHNICAL FIELD

The disclosure herein relates to X-ray applications, particularly relates to X-ray imaging with a detector capable of resolving photon energy.

BACKGROUND

X-ray has been used to form an image of an object in medical and industrial applications. In one application, an X-ray microscope is an instrument used to produce enlarged images of samples illuminated with X-rays. There are two main types of microscopes: full field microscopes and scanning microscopes. In full field microscopes, the whole field of view is imaged to a detector plane at the same time. In scanning microscopes, the sample is illuminated with a bright well focused spot scanning over the sample.

FIG. 1 schematically shows a conventional X-ray microscope with focusing optical elements. As shown in FIG. 1, the conventional X-ray microscope includes an X-ray point source 101, a focusing optics 104, and a detector for the resulting X-ray image 103 of the sample 102. In practice, the point source is not very small (>5 microns), and thus the resulting image is not very sharp. Therefore, the focusing optics 104 is needed to focus X-ray from the X-ray point source 101 into a tiny virtual source 105. The focusing optics 104 may be a Fresnel zone plate. The magnification of the set-up is the quotient L2/L1 with the distance source-sample L1 and the distance source-image L2.

Fresnel zone plate, like most refractive optics that can be used as the focusing optics 104, has chromatic aberration. Therefore, focal lengths of the Fresnel zone plate are different for X-rays with different wavelengths or frequencies. To avoid chromatic aberration in X-ray imaging, a conventional solution is to use a microfocus X-ray source that is monochromatic. A monochromatic microfocus X-ray source may be produced with microfocus tubes. But this requires a very efficient filter, which is difficult to achieve for X-ray, where useful X-ray photons may be lost.

X-ray computed tomography (CT) is another application of X-ray image, using X-rays to create cross-sections of an object that can be used to recreate a virtual model, e.g. a three-dimension (3D) mode, without destroying the original object. X-ray microtomography or micro-computed tomography (micro-CT) is X-ray CT when the pixel sizes of the cross-sections are usually in the micrometer range.

FIG. 2 schematically shows a conventional X-ray CT system. As shown in FIG. 2, the X-ray CT system in FIG. 2 includes an X-ray source 201, a capillary condenser 202, an objective zone plate 204, a phase plate 205, and a charge-coupled device (CCD) detector 206. The sample 203 is placed at the focal point of the X-ray. This system in FIG. 2 is capable of phase-contrast CT.

Since the capillary condenser 202 can condense X-rays of all wavelengths into a focal point in the nanometer range, there is no need for a filter before the sample. However, an X-ray CT system like this in FIG. 2 is bulky and expensive, and includes a very complicated optical path.

SUMMARY

Disclosed herein is an X-ray microscope, comprising: an X-ray source configured to irradiate a sample with X-ray; and a detector configured to: detect X-ray photons from the sample, determine energy of the detected X-ray photons, and generating an image of the sample based on the detected X-ray photons that have energies in a predetermined range.

According to an embodiment, the X-ray photons from the sample comprise X-ray photons having energies in the predetermined range and X-ray photons having energies outside the predetermined range.

According to an embodiment, the X-ray microscope further comprises focusing optics configured to focus the X-ray from the X-ray source into a virtual point source before the sample.

According to an embodiment, the detector is further configured to determine a number of the detected X-ray photons that have energies in the predetermined range.

According to an embodiment, the detector comprises an array of pixels; and the detector is further configured to determine a number of the detected X-ray photons that have energies in the predetermined range, for each of the pixels.

According to an embodiment, the detector is a semiconductor X-ray detector.

According to an embodiment, the detector is further configured to: determine a first number of X-ray photons that are detected by the detector and have energies in a first range; and determine a second number of X-ray photons that are detected by the detector and have energies in a second range.

According to an embodiment, the detector is further configured to generate a first image of the sample based on the first number of X-ray photons and a second image of the sample based on the second number of X-ray photons.

Disclosed herein is an X-ray computed tomography (CT) system, comprising: an X-ray source configured to irradiate an object with X-ray; and a detector configured to: detect X-ray photons from the object, determine energy of the detected X-ray photons, and reconstruct a virtual model of the object based on detected X-ray photons that have energies in a predetermined range.

According to an embodiment, the X-ray photons from the object comprise X-ray photons having energies in the predetermined range and X-ray photons having energies outside the predetermined range.

According to an embodiment, the detector is further configured to determine a number of the detected X-ray photons that have energies in the predetermined range.

According to an embodiment, the detector comprises an array of pixels; and the detector is further configured to determine a number of the detected X-ray photons that have energies in the predetermined range, for each of the pixels.

According to an embodiment, the detector is a semiconductor X-ray detector.

According to an embodiment, the detector is further configured to: determine a first number of X-ray photons that are detected by the detector and have energies in a first range; and determine a second number of X-ray photons that are detected by the detector and have energies in a second range.

According to an embodiment, the detector is further configured to reconstruct a virtual model of the object based on the first number of X-ray photons and the second number of X-ray photons.

Disclosed herein is a system comprising: an X-ray source configured to irradiate an object with X-ray; a condenser; and a detector configured to determine energy of the detected X-ray photons and determine energy of the detected X-ray photons, wherein the system is configured for performing X-ray microtomography with respect to the object.

According to an embodiment, the system is configured to recreate a virtual model of the object or forming an image of the object by measuring energy of X-ray photons that are irradiated by the X-ray source, affected by the object, and detected by the detector.

According to an embodiment, the detector is further configured to: determine a first number of X-ray photons that are detected by the detector and have energies in a first range; and determine a second number of X-ray photons that are detected by the detector and have energies in a second range.

According to an embodiment, the X-ray source emits X-rays with a first spectral line and a second spectral line; the X-ray with the first spectral line includes photons having energies in the first range; and the X-ray with the second spectral line includes photons having energies in the second range.

According to an embodiment, the X-ray with the first spectral line forms a first focal point by the condenser; the X-ray with the second spectral line forms a second focal point by the condenser; and the object is placed between the first focal point and the second focal point, when being irradiated by the X-rays.

Disclosed herein is a method, comprising: irradiating a sample with X-ray; detecting a first plurality of X-ray photons from the sample, at a first distance from the sample; determining energy of the first plurality of X-ray photons; and generating a first image of the sample based on the first plurality of X-ray photons that have energies in a predetermined range.

According to an embodiment, the first plurality of X-ray photons from the sample comprise X-ray photons having energies in the predetermined range and X-ray photons having energies outside the predetermined range.

According to an embodiment, the method further comprises focusing the irradiated X-ray from the X-ray source into a virtual X-ray point source before the sample.

According to an embodiment, generating the image is performed by a detector comprising a plurality of pixels and generating the image further comprises: determining a plurality of numbers, a number of the first plurality of detected X-ray photons that have energies in the predetermined range, for each of the pixels; and generating the image of the sample based on the number.

According to an embodiment, the method further comprises determining a first number of X-ray photons that are detected and have energies in a first range; and determining a second number of X-ray photons that are detected and have energies in a second range.

According to an embodiment, the method further comprises generating a first image of the sample based on the first number of X-ray photons and a second image of the sample based on the second number of X-ray photons.

According to an embodiment, the method further comprises detecting a second plurality of X-ray photons from the sample, at a second distance from the sample; determining energy of the second plurality of X-ray photons; and generating a second image of the sample based on the second plurality of X-ray photons that have energies in a predetermined range.

Disclosed herein is a method, comprising: irradiating an object with X-ray; detecting X-ray photons from the object; determining energy of the detected X-ray photons; and reconstructing a virtual model of the object based on detected X-ray photons that have energies in a predetermined range.

According to an embodiment, the method further comprises determining a first number of X-ray photons that are detected and have energies in a first range; and determining a second number of X-ray photons that are detected and have energies in a second range.

According to an embodiment, the reconstructing is based on the first number of X-ray photons and the second number of X-ray photons.

BRIEF DESCRIPTION OF THE DRAWINGS

FIG. 7A schematically shows a cross-sectional view of a detector, according to an embodiment of the present teaching;

FIG. 10A schematically shows a system suitable for phase-contrast X-ray imaging (PCI), according to an embodiment of the present teaching;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

In the present teaching, a detector capable of resolving photon energy is used in X-ray imaging. In one embodiment, the detector can resolve energy of each photon absorbed by the detector. Based on the resolved energy, the detector can determine wavelength and frequency of the photon. The detector may count the number of photons of interest, e.g. photons having wavelengths in a given range. As such, there is no need for a complicated monochromatic X-ray source.

The detector in the present teaching may be a semiconductor X-ray detector that is cheap to produce and can simplify the optical path in X-ray imaging. For example, in a microscope, the semiconductor X-ray detector can have a large surface (e.g. >1 square centimeter) for absorbing X-ray, due to its low cost. As such, there is no need for complicated optical devices between the sample and the detector.

When an X-ray photon is absorbed in a semiconductor layer of an X-ray detector having an array of pixels, multiple charge carriers (e.g., electrons and holes) are generated and may be swept under an electric field towards circuitry for measuring these charge carriers. According to an embodiment, when an X-ray photon is collected by a pixel, the detector may determine energy of the X-ray photon based on a voltage detected from the pixel. For each pixel, the detector can then determine the number of X-ray photons that are collected by the pixel and have energies within a given range. By compiling the numbers together, the detector may generate an image at a wavelength corresponding to the energy range. Similarly, the detector can simultaneously generate multiple images each of which corresponds to a different X-ray wavelength. The multiple images may be integrated to generate a color image of the sample. A "color" image as used in the context of X-ray imaging means an image containing information obtained from X-ray of more than one wavelength.

Therefore, the detector in the present teaching can simplify the structure of an X-ray imaging system (e.g. a microscope, a micro-CT system, etc.) and lower its cost, without losing its imaging efficiency.

Figure 1:
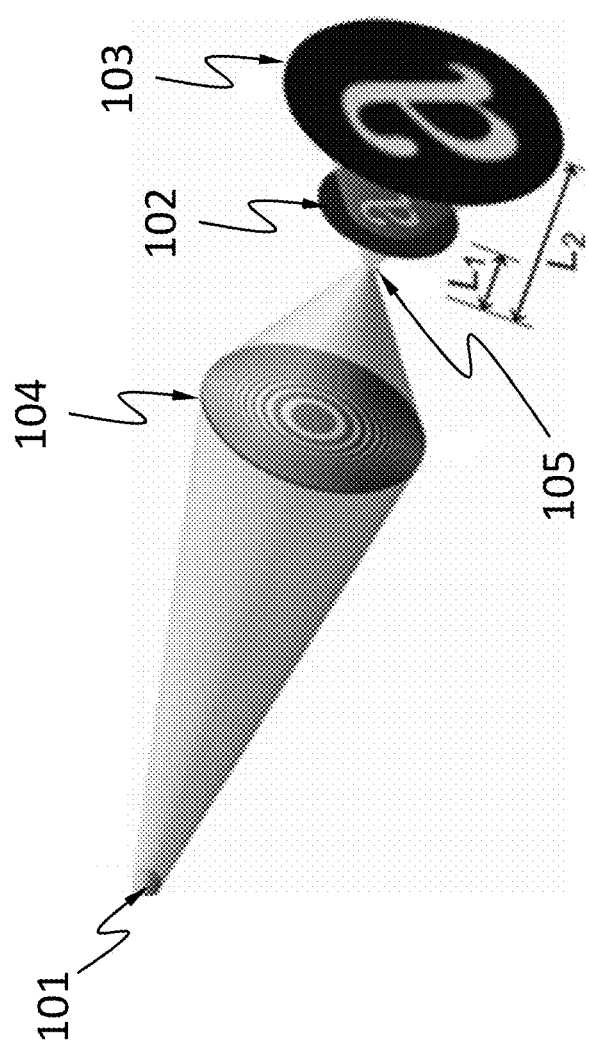
FIG. 1 schematically shows a conventional X-ray microscope with focusing optical elements.
Figure 2:
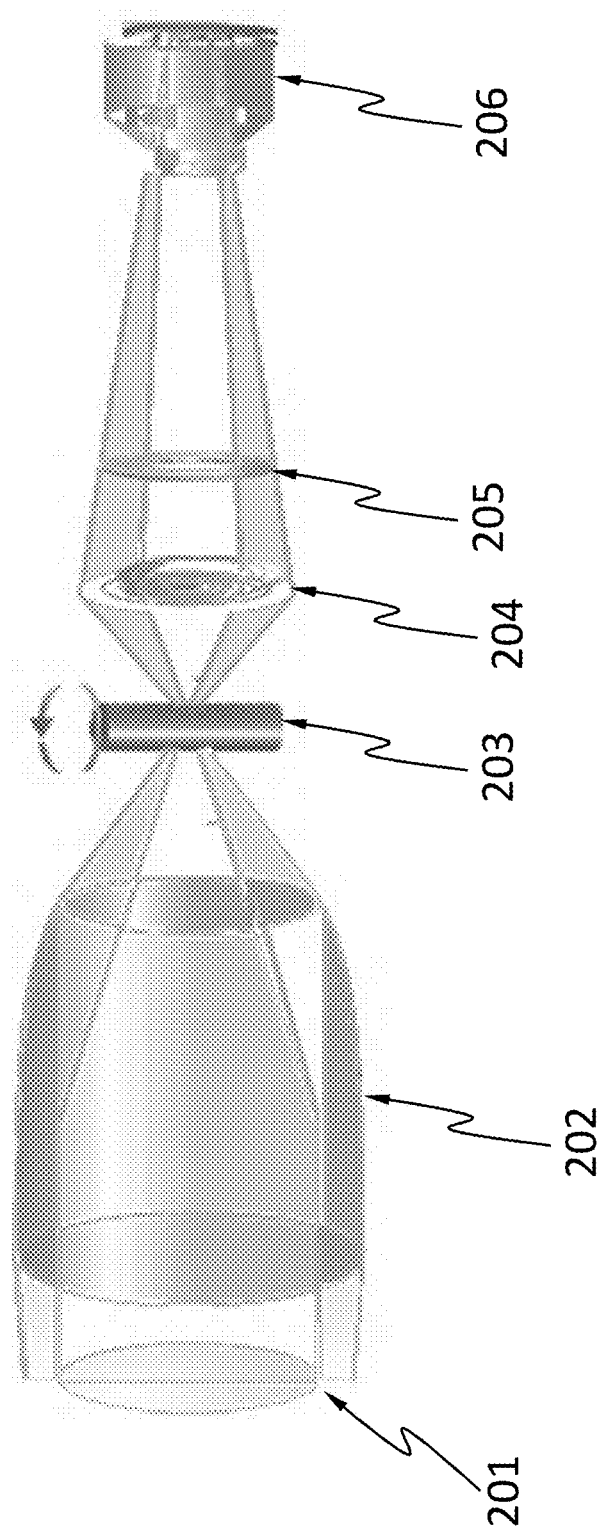
FIG. 2 schematically shows a conventional X-ray CT system.
Figure 3:
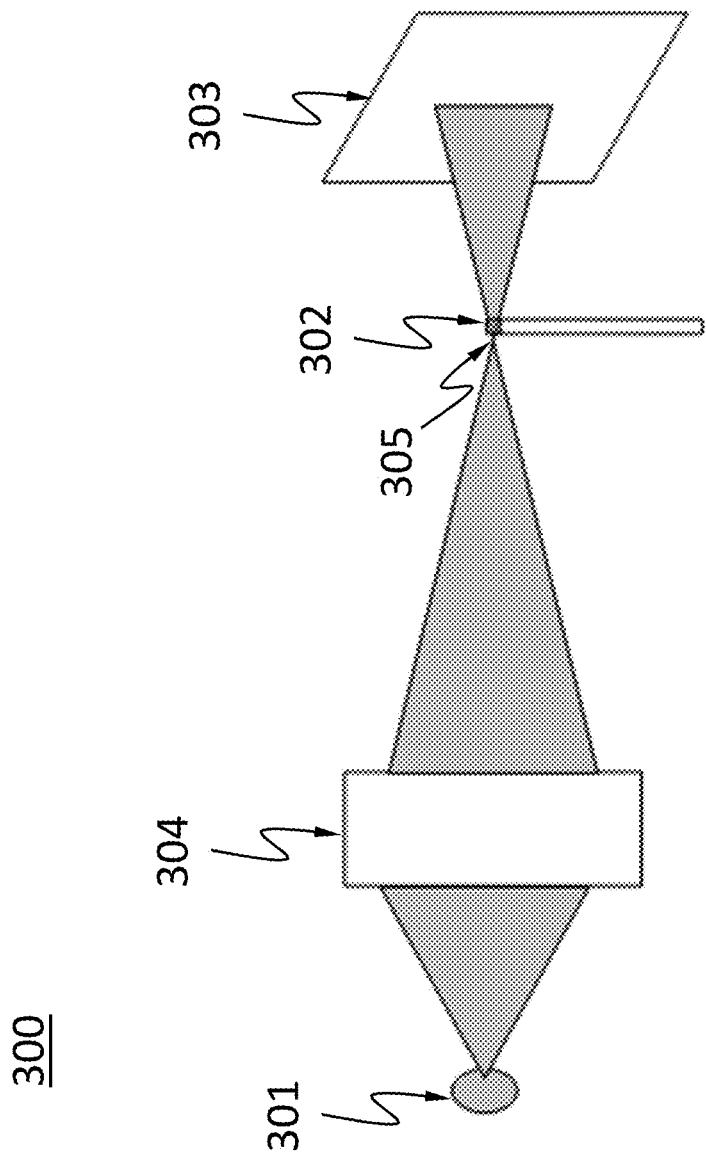
FIG. 3 schematically shows an X-ray microscope, according to an embodiment of the present teaching.

FIG. 3 schematically shows an X-ray microscope 300, according to an embodiment of the present teaching. The X-ray microscope 300 may include an X-ray source 301, a focusing optics 304, and a detector 303 for detecting the resulting X-ray image of the sample 302.

According to an embodiment, the X-ray source 301 may be a microfocus X-ray source with a size of 5 to 20 μm. The focusing optics 304 may help to focus the X-ray irradiated from the X-ray source 301 into a focal point 305, which forms a tiny virtual source. According to an embodiment, the focal point 305 has a size of 1 to 100 nm.

In one example, the focusing optics 304 may be a Fresnel zone plate. A Fresnel zone plate, like most refractive optics that can be used as the focusing optics 304, has chromatic aberration. Therefore, focal lengths of the Fresnel zone plate are different for X-rays with different wavelengths or frequencies. In this case, the focal point 305 is determined with respect to X-rays with a predetermined wavelength or a predetermined small range of wavelengths.

In another example, the focusing optics 304 may be a focusing optics based on multi-reflections. In this case, the focal point 305 is determined with respect to X-rays with all wavelengths of interest.

According to an embodiment, the sample 302 may be a piece of life organ or tissue, with a thickness of 100 μm or below. The sample 302 may be placed close to the focal point 305, either on the side closer to the detector 303 as shown in FIG. 3, or on the side closer to the X-ray source 301. For single color imaging, the sample 302 may be placed between the focal point 305 and the detector 303, to achieve an upright and clear image of the sample ("single color imaging" used in the present teachings means imaging based on X-rays of a wavelength or a small range of wavelengths). Some pre-process of the sample 302 may be performed to fix the sample 302 and make sure that the structure of the sample 302 does not change under irradiation of X-ray.

According to an embodiment, the detector 303 may be a semiconductor X-ray detector, with a size of 10 to 100 mm. For single color imaging, the detector 303 may detect photons that have energies in a predetermined range of interest, even if the X-ray source 301 is not monochromatic. For example, the detector 303 may only count the number of X-ray photons that are absorbed by the detector 303 and have energies E within a given range.

The energy E of a photon depends only on its frequency (ν) or inversely, its wavelength (λ), based on the following equation:

$$E=h\nu=hc/\lambda,$$

where h represents the Planck constant; c represents the speed of light. Therefore, by selecting the energy of X-rays for counting, the detector 303 selects the corresponding wavelength for imaging.

According to an embodiment, the detector 303 may determine energy of an absorbed X-ray photon by measuring a voltage of an electrode in the detector 303, caused by the absorbed X-ray photon. In one example, the detector 303 can measure the energy of the photon with a measurement error of less than 150 eV. The term "measure" or "measurement" as used herein with respect to voltage or energy is not limited to ascertaining the exact value of the voltage or energy, but includes determining whether the value of the voltage or energy falls within a given range. Therefore, for each absorbed X-ray photon, based on the measured voltage, the detector 303 can determine energy of the absorbed X-ray photon, and thus determine its wavelength. If the wavelength is within a predetermined range of interest, the detector 303 will increase the number of interested photons by one. Otherwise, the detector 303 will ignore. Thus, the present teaching does not need a complicated monochromatic X-ray source that irradiates only X-rays with a single wavelength or within a small range of wavelengths.

For an X-ray detector having an array of pixels, the energy resolving and photon counting may be performed at each pixel. According to an embodiment, when an X-ray photon is collected by a pixel, the detector 303 may determine energy of the X-ray photon based on a voltage detected from the pixel. For each pixel, the detector 303 can then determine the number of X-ray photons that are collected by the pixel and have energies within a given range, i.e. having wavelengths within a corresponding range. For example, over a period of time, pixel i counted $n_i$ photons with wavelength $\lambda$, where i=1 ... N, and N represents the number of pixels of the detector 303. By compiling the numbers of photons at each pixel with wavelength $\lambda$, the detector 303 may generate an image at wavelength $\lambda$. From the image, the effect (e.g., absorption, refraction, diffraction) on X-ray by the sample 302 at wavelength $\lambda$ can be derived.

Similarly, the detector 303 can simultaneously generate multiple images each of which corresponds to a different X-ray wavelength. By selecting different energy ranges or different voltage ranges, the detector 303 may form images at different X-ray wavelengths. Thus, the detector 303 can generate a color image of the sample 302 based on the images at different X-ray wavelengths.

According to an embodiment, the focusing optics 304 may include the capillary condenser 202. The capillary condenser 202 can condense X-rays of all wavelengths to a single focal point before irradiating the sample 302. After the sample 302 is irradiated by the X-rays, the X-rays of different wavelengths can be differentiated by different absorption rates and/or different refraction rates when passing through the sample 302. In this embodiment, the detector 303 can derive refraction of X-rays at different wavelengths, e.g. by resolving energies of the X-rays of different wavelengths or different colors. With the derived refractions, the detector 303 may obtain a true-color 3D-distribution of the real part of the refractive index of the object, e.g. based on a reconstruction algorithm and phase-contrast X-ray imaging (PCI) (PCI can be implemented by taking two images at two different distances from the sample).

Based on a magnification target for the result image, the system can select a distance between the sample 302 and the detector 303 and a distance between the sample 302 and the focal point 305. In one example, the distance between the sample 302 and the detector 303 is in the 10 to 100 cm range; and the distance between the sample 302 and the focal point 305 is in the 100 μm to 10 mm range.

Figure 4:
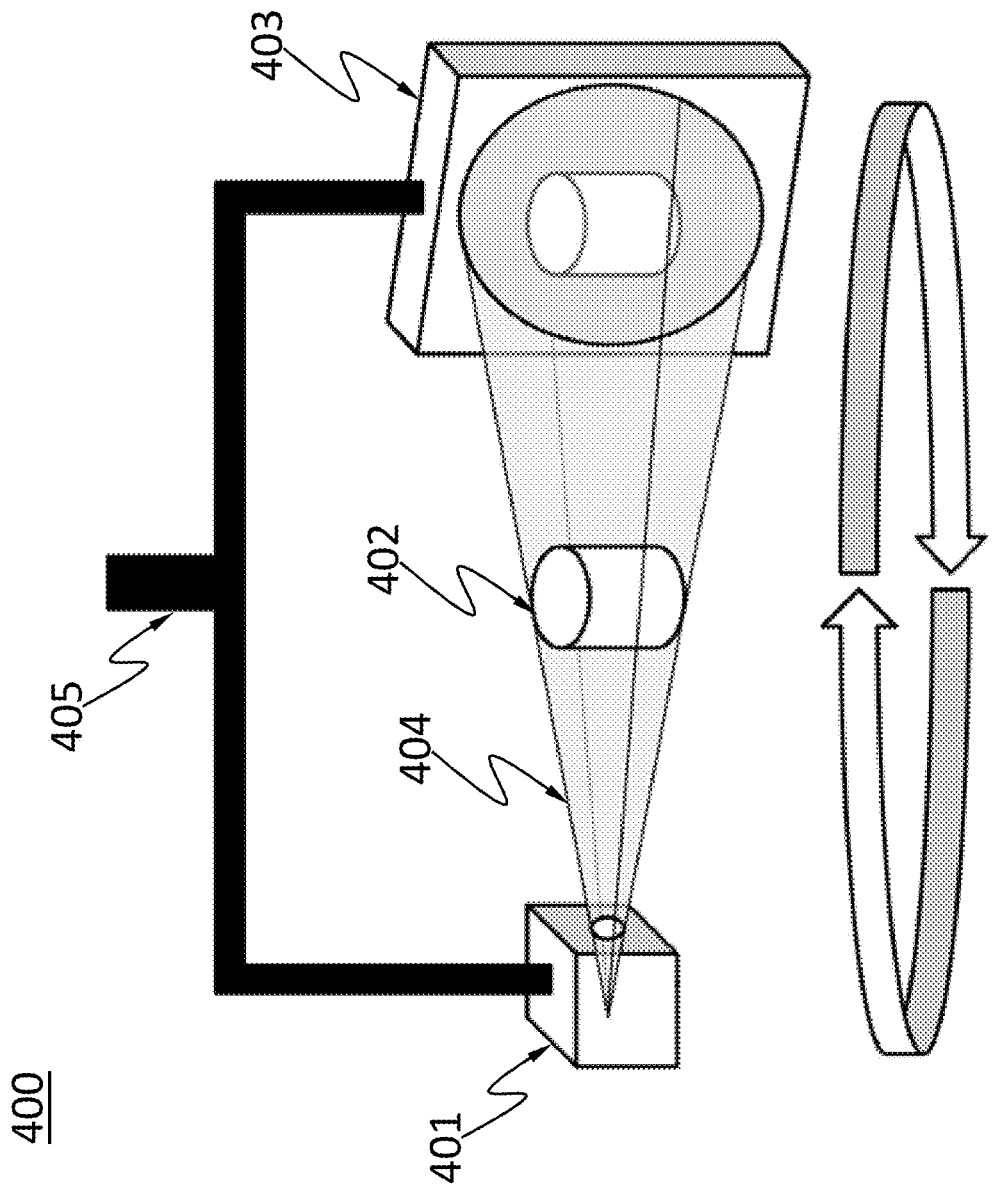
FIG. 4 schematically shows an X-ray CT system, according to an embodiment of the present teaching.

FIG. 4 schematically shows an X-ray CT system 400, according to an embodiment of the present teaching. The X-ray CT system 400 may be a cone beam CT (CBCT) system, where the X-rays used for CT are divergent and forming a cone. A CBCT system may be used in medical imaging, e.g. in orthodontics.

As shown in FIG. 4, the 400 includes an X-ray beam source 401 that may irradiate a conical beam 404 towards an object 402, which results in an image detected by a detector 403. In this example, the 401 and the 403 are physically connected, e.g. by two mechanical arms, such that the 401 and the 403 can rotate around a rotational axis 405. As such, the 400 may obtain different images of the object, by rotating the 401 and the 403 around the object. Each of the images is a projection image of the 402 at a particular degree of rotation. The detector 403 may collect data from the projection images and reconstruct a 2D image or 3D model of the 402. For example, the detector can produce what is termed a digital volume composed of three-dimensional voxels of anatomical data that can then be manipulated and visualized with specialized software.

In one embodiment, the 401 may correspond to the focal point 305 that is formed by the 301 and the 304. In another embodiment, the 403 may resolve X-ray photon energy like the 303.

Figure 5:
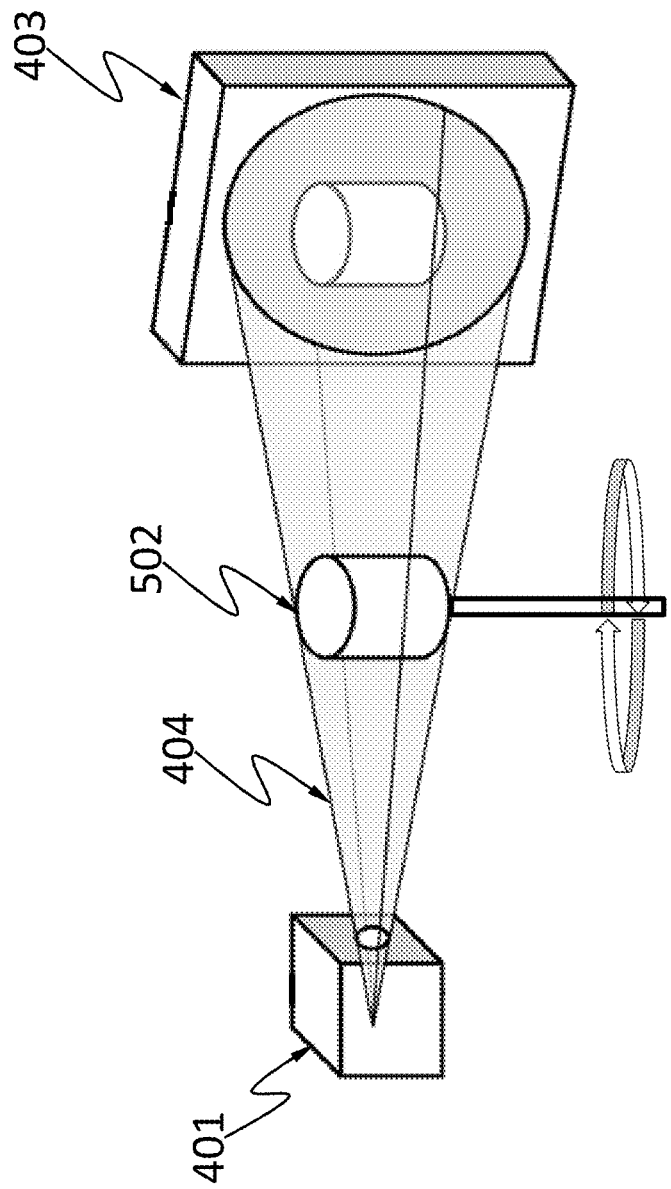
FIG. 5 schematically shows another X-ray CT system, according to an embodiment of the present teaching.

FIG. 5 schematically shows another X-ray CT system 500, according to an embodiment of the present teaching. The X-ray CT system 500 may be a CBCT system similar to the 400, except that the 401 and the 403 are fixed and not necessarily physically connected, while an object 502 may be rotated during scanning. As such, the 500 may obtain different projection images of the object 502, by rotating the 502 during scanning. As discussed before, the detector 403 may collect data from the projection images and reconstruct a 2D image or 3D model of the 502. In one embodiment, the 401 may correspond to the focal point 305 that is formed by the 301 and the 304. In another embodiment, the 403 may resolve X-ray photon energy like the 303.

Figure 6:
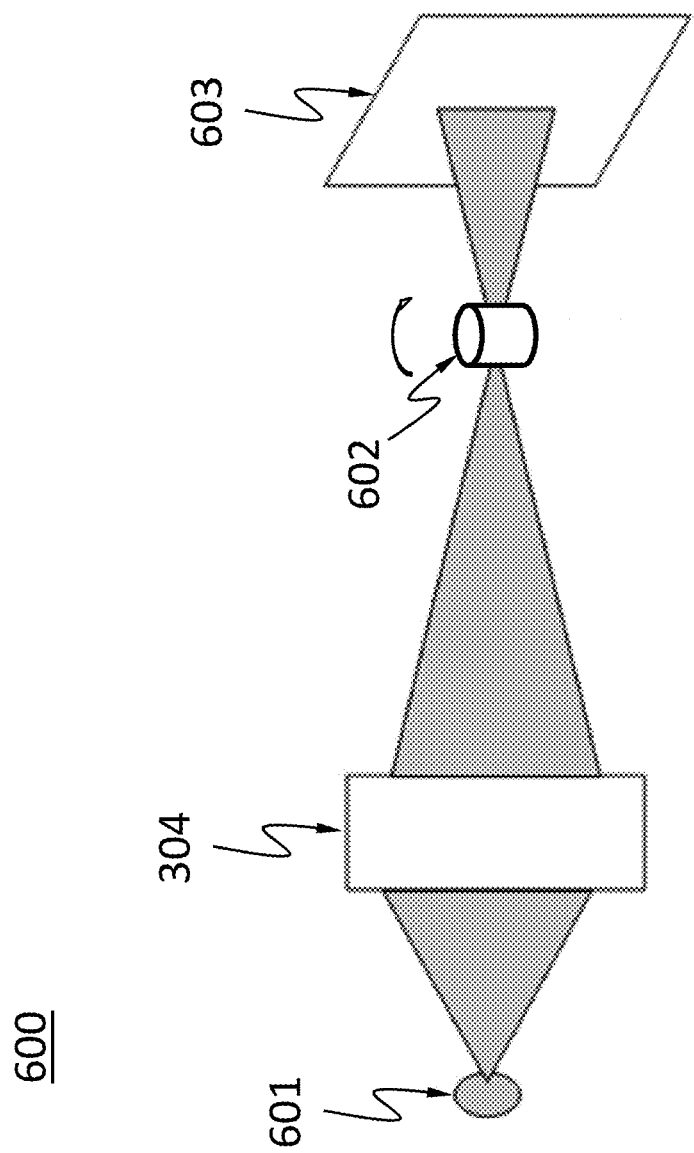
FIG. 6 schematically shows an X-ray micro-CT system, according to an embodiment of the present teaching.

FIG. 6 schematically shows an X-ray micro-CT system 600, according to an embodiment of the present teaching. The system 600 may include an X-ray source 601, the focusing optics 304, and a detector 603 for detecting the resulting X-ray image of the sample 602.

According to an embodiment, the X-ray source 601 may be a microfocus X-ray source like the 301; the 603 may resolve X-ray photon energy like the 303; and the focusing optics 304 (e.g. a Fresnel zone plate) may help to focus the X-ray irradiated from the X-ray source 601 into a focal point, which forms a tiny virtual source.

According to an embodiment, the sample 602 may be a piece of human bone like a tooth or a commercial product like a diamond. When the sample 602 is large, the sample 602 may be placed such that the region of interest of the sample 602 is centered in the field of view for the beam.

In this example, the sample 602 may rotate relative to the X-ray source 601 and the beam, such that the system 600 may scan the sample 602 from different angles, and obtain different images of the object. The detector 603 may collect data from the images and reconstruct a 2D image or 3D model of the sample 602.

Figure 7B:
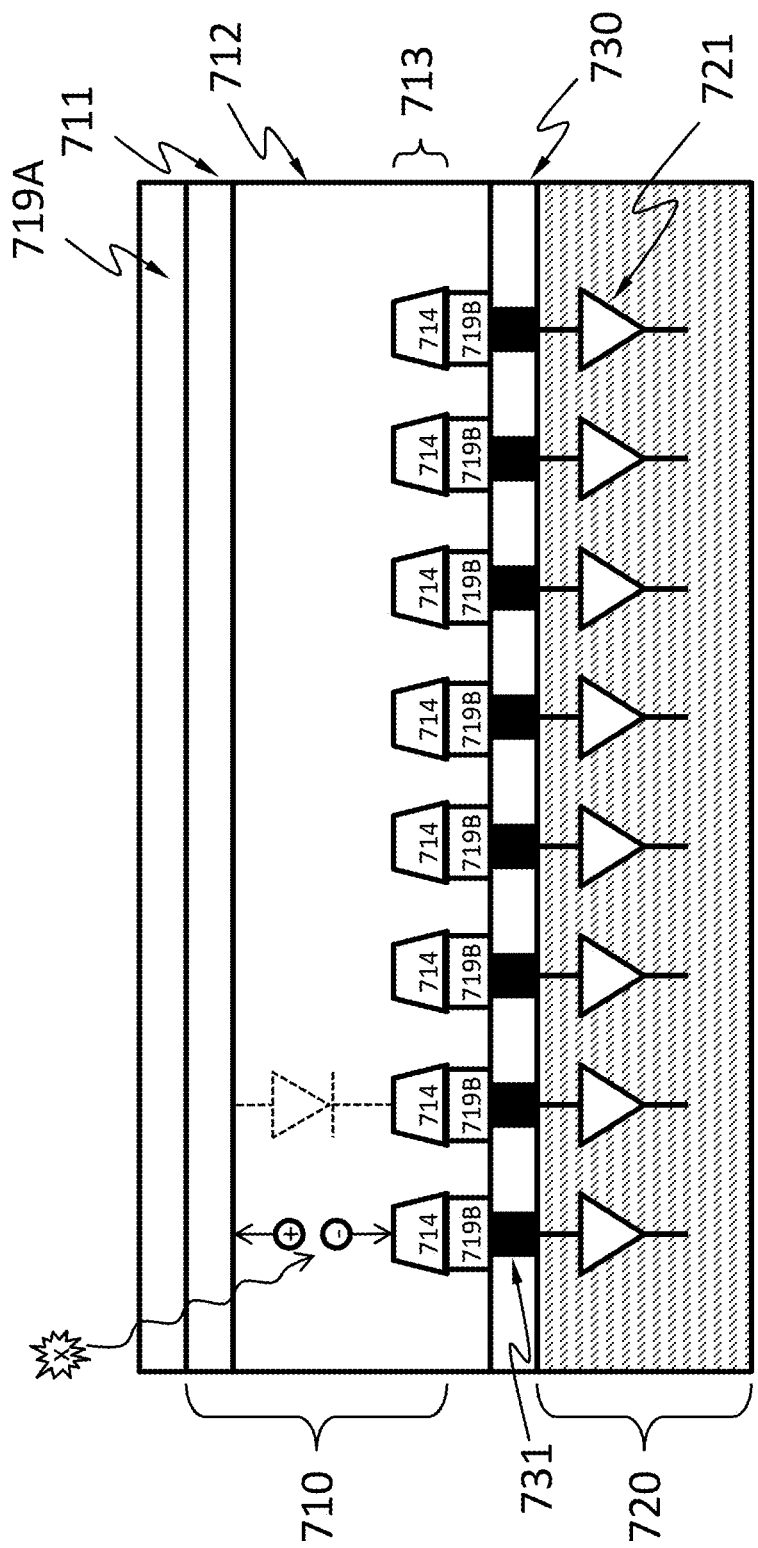
FIG. 7B schematically shows a detailed cross-sectional view of the detector, according to an embodiment of the present teaching.

FIG. 7A schematically shows a cross-sectional view of a detector 700 that can be used in the X-ray microscope 300, the X-ray CT system 400, the X-ray CT system 500, or the X-ray micro-CT system 600, according to an embodiment of the present teaching. One skilled in the art can understand that the structure of the detector 700 shown in FIGS. 7A-7D is just for purpose of an exemplary illustration, and any detector that can resolve energy of an X-ray photon may be used in the X-ray microscope 300, the X-ray CT system 400, the X-ray CT system 500, and the X-ray micro-CT system 600.

The detector 700 may be a semiconductor X-ray detector including an X-ray absorption layer 710 and an electronics layer 720 (e.g., an ASIC) for processing or analyzing electrical signals incident X-ray generates in the X-ray absorption layer 710. The X-ray absorption layer 710 may include a semiconductor material such as, silicon, germanium, GaAs, CdTe, CdZnTe, or a combination thereof. The semiconductor may have a high mass attenuation coefficient for the X-ray energy of interest.

As shown in a detailed cross-sectional view of the detector 700 in FIG. 7B, according to an embodiment, the X-ray absorption layer 710 may include one or more diodes (e.g., p-i-n or p-n) formed by a first doped region 711, one or more discrete regions 714 of a second doped region 713. The second doped region 713 may be separated from the first doped region 711 by an optional the intrinsic region 712. The discrete portions 714 are separated from one another by the first doped region 711 or the intrinsic region 712. The first doped region 711 and the second doped region 713 have opposite types of doping (e.g., region 711 is p-type and region 713 is n-type, or region 711 is n-type and region 713 is p-type). In the example in FIG. 7B, each of the discrete regions 714 of the second doped region 713 forms a diode with the first doped region 711 and the optional intrinsic region 712. Namely, in the example in FIG. 7B, the X-ray absorption layer 710 has a plurality of diodes having the first doped region 711 as a shared electrode. The first doped region 711 may also have discrete portions.

When an X-ray photon hits the X-ray absorption layer 710 including diodes, the X-ray photon may be absorbed and generate one or more charge carriers by a number of mechanisms. The charge carriers may drift to the electrodes of one of the diodes under an electric field. The field may be an external electric field. The electrical contact 719B may include discrete portions each of which is in electrical contact with the discrete regions 714.

Figure 7C:
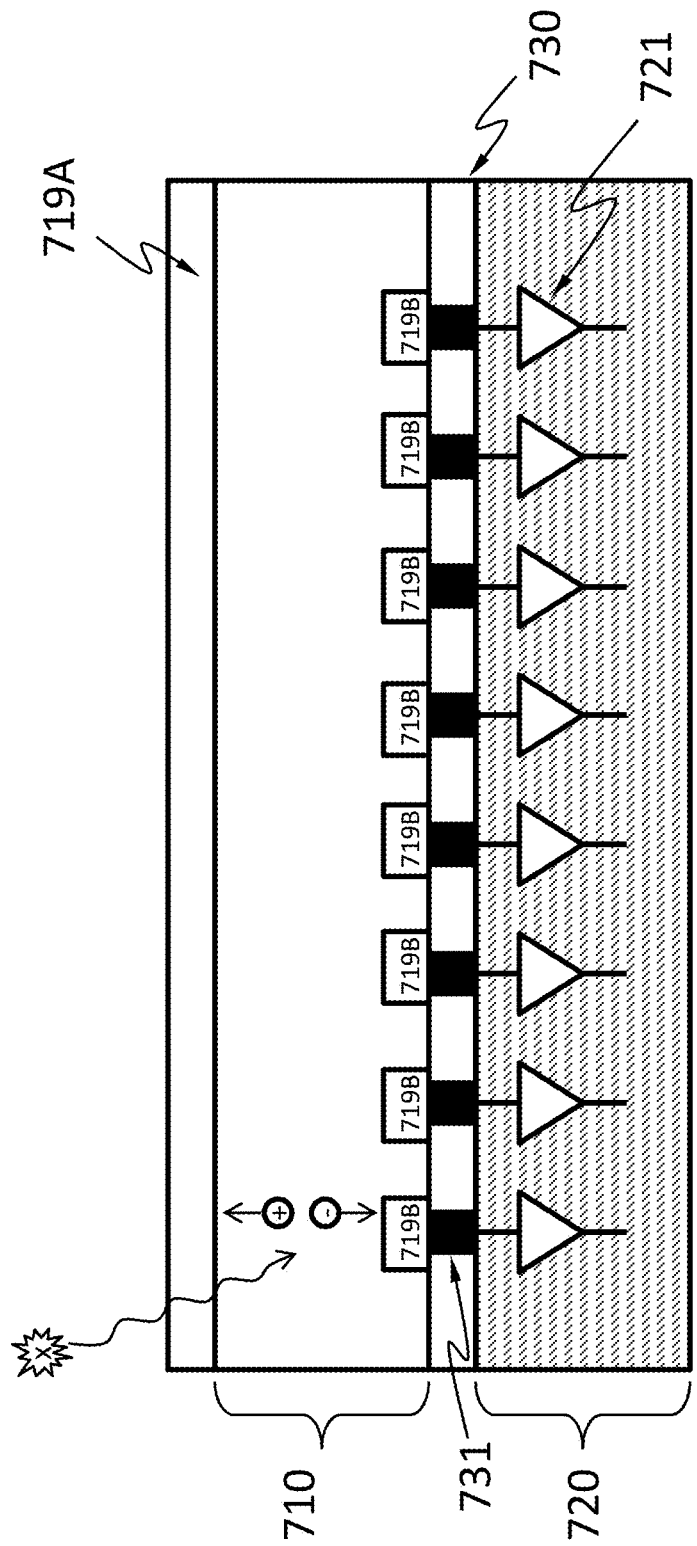
FIG. 7C schematically shows an alternative detailed cross-sectional view of the detector, according to an embodiment of the present teaching.

As shown in an alternative detailed cross-sectional view of the detector 700 in FIG. 7C, according to an embodiment, the X-ray absorption layer 710 may include a resistor of a semiconductor material such as, silicon, germanium, GaAs, CdTe, CdZnTe, or a combination thereof, but does not include a diode.

When an X-ray photon hits the X-ray absorption layer 710 including a resistor but not diodes, it may be absorbed and generate one or more charge carriers by a number of mechanisms. The charge carriers may drift to the electrical contacts 119A and 119B under an electric field. The electrical contact 719B includes discrete portions.

The electronics layer 720 may include an electronic system 721 suitable for processing or interpreting signals generated by X-ray photons incident on the X-ray absorption layer 710. The electronic system 721 may include an analog circuitry such as a filter network, amplifiers, integrators, and comparators, or a digital circuitry such as a microprocessors, and memory. The electronic system 721 may include components shared by the pixels or components dedicated to a single pixel. For example, the electronic system 721 may include an amplifier dedicated to each pixel and a microprocessor shared among all the pixels. The electronic system 721 may be electrically connected to the pixels by vias 731. Space among the vias may be filled with a filler material 730, which may increase the mechanical stability of the connection of the electronics layer 720 to the X-ray absorption layer 710. Other bonding techniques are possible to connect the electronic system 721 to the pixels without using vias.

Figure 7D:
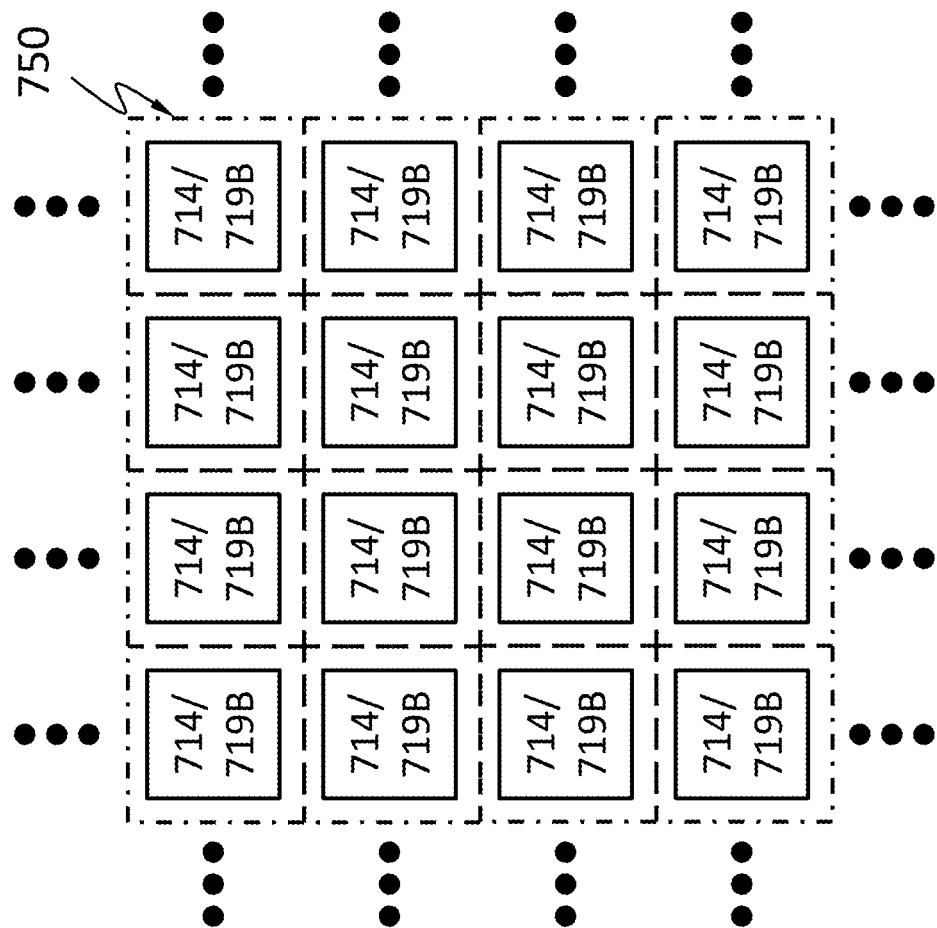
FIG. 7D shows an exemplary top view of a portion of the detector, according to an embodiment of the present teaching.

FIG. 7D shows an exemplary top view of a portion of the semiconductor X-ray detector 700 with a 4-by-4 array of discrete regions 714/719B. Charge carriers generated by an X-ray photon incident around the footprint of one of these discrete regions 714/719B are not substantially shared with another of these discrete regions 714/719B. The area 750 around a discrete region 714/419B in which substantially all (more than 95%, more than 98% or more than 99% of) charge carriers generated by an X-ray photon incident therein flow to the discrete region 714/419B is called a pixel associated with that discrete region 714/419B. Namely, less than 5%, less than 2% or less than 1% of these charge carriers flow beyond the pixel, when the X-ray photon hits inside the pixel. By measuring the rate of change of the voltage of each of the discrete regions 714/719B, the number of X-ray photons absorbed (which relates to the incident X-ray intensity) and/or the energies thereof in the pixels associated with the discrete regions 714/719B may be determined. Thus, the spatial distribution (e.g., an image) of incident X-ray intensity may be determined by individually measuring the rate of change of the voltage of each one of an array of discrete regions 714/719B. The pixels may be organized in any suitable array, such as, a square array, a triangular array and a honeycomb array. The pixels may have any suitable shape, such as, circular, triangular, square, rectangular, and hexangular. The pixels may be individually addressable.

Figure 8:
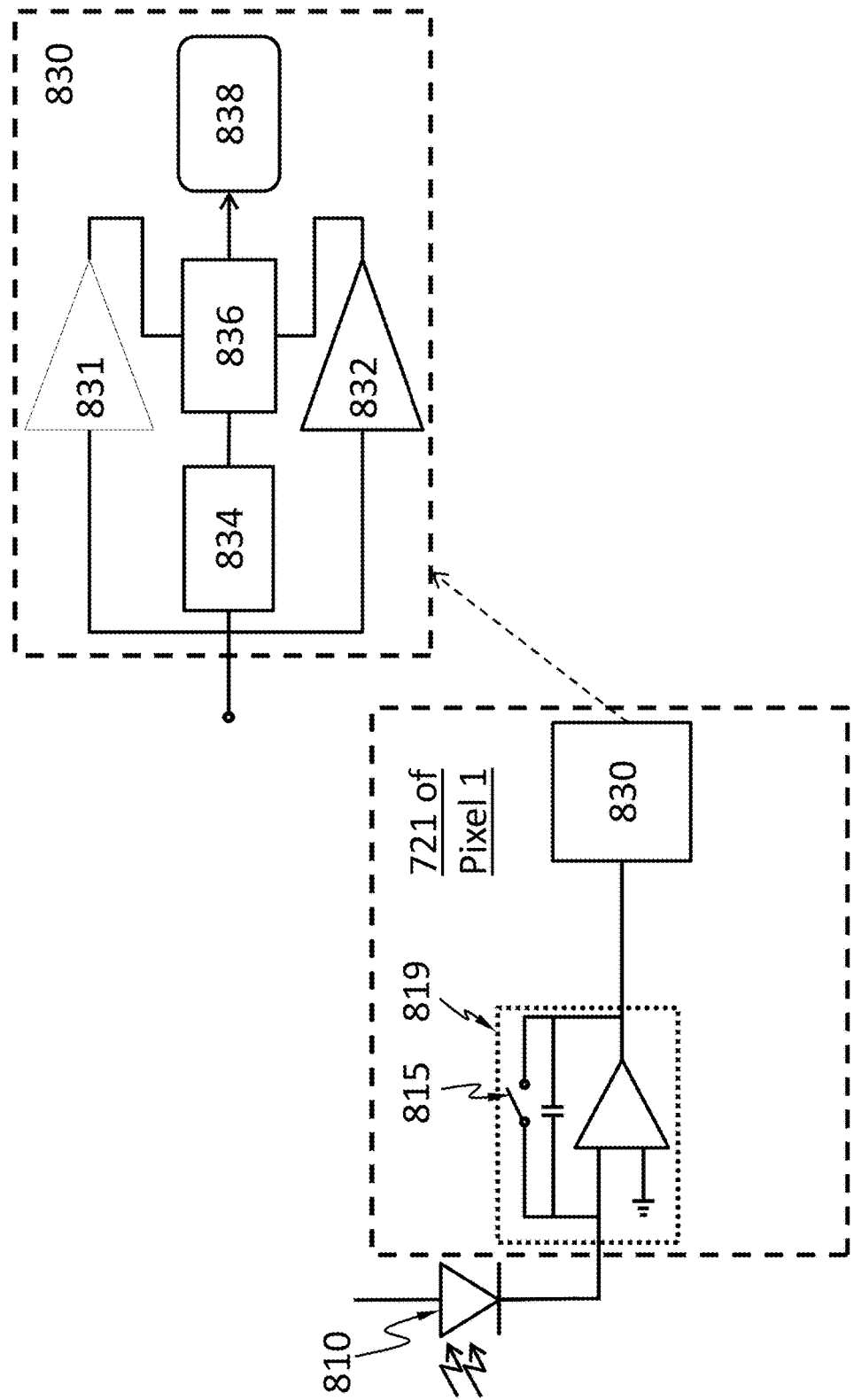
FIG. 8 shows component diagrams of an electronic system of a semiconductor X-ray detector, according to an embodiment of the present teaching.

FIG. 8 shows component diagrams of an electronic system 721 of a semiconductor X-ray detector, according to an embodiment of the present teaching. As shown in FIG. 8, the electronic system 721 of Pixel 1 is configured for processing signals from an electrode of a diode 810 in Pixel 1.

In this example, the electronic system 721 of Pixel 1 may include a capacitor module 819, and a data processing module 830. As shown in FIG. 8, the capacitor module 819 is electrically connected to the electrode of the diode 810 or the electrical contact. The capacitor module 819 is configured to collect charge carriers from the electrode. The capacitor module 819 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode may accumulate on the capacitor over a period of time ("integration period"). After the integration period has expired, the capacitor voltage is sampled and then reset by a reset switch 815. The capacitor module 819 can include a capacitor directly connected to the electrode.

The electronic system 721 in FIG. 6 may comprise the data processing module 830 that may include downstream circuits for interpreting and processing signal from upstream of the electronic system 721.

According to an embodiment, the data processing module 830 includes a first voltage comparator 831, a second voltage comparator 832, a counter 838, a voltmeter 834 and a controller 836.

The first voltage comparator 831 is configured to compare a voltage (e.g. a voltage of an electrode of a diode 810) to a first threshold. The diode may be a diode formed by the first doped region 711, one of the discrete regions 714 of the second doped region 713, and the optional intrinsic region 712. Alternatively, the first voltage comparator 831 is configured to compare the voltage of an electrical contact (e.g., a discrete portion of electrical contact 719B) to a first threshold. The first voltage comparator 831 may be configured to monitor the voltage directly, or calculate the voltage by integrating an electric current flowing through the diode or electrical contact over a period of time. The first voltage comparator 831 may be controllably activated or deactivated by the controller 836.

The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 710, and other factors. For example, the first threshold may be 50 mV, 100 mV, 150 mV, or 200 mV.

The second voltage comparator 832 is configured to compare a voltage (e.g. a voltage of an electrode of a diode 810) to a second threshold. The second voltage comparator 832 may be configured to monitor the voltage directly, or calculate the voltage by integrating an electric current flowing through the diode or the electrical contact over a period of time. The second voltage comparator 832 may be controllably activate or deactivated by the controller 836. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 832 and the first voltage comparator 310 may be the same component. Namely, the system 721 may have one voltage comparator that can compare a voltage with two different thresholds at different times.

The counter 838 is configured to register a number of X-ray photons reaching a corresponding diode or resistor. The counter 838 may be a software component (e.g., a number stored in a computer memory) or a hardware component (e.g., a 4017 IC and a 7490 IC). In one embodiment, the counter 838 may register a number of X-ray photons that reach a corresponding diode or resistor and meet a condition, e.g. having energies within a given range or having wavelengths within a given range.

The controller 836 may be a hardware component such as a microcontroller and a microprocessor. The controller 836 may be configured to start a time delay from a time at which the first voltage comparator 831 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 836 may be configured to keep deactivated the second voltage comparator 832, the counter 838 and any other circuits the operation of the first voltage comparator 831 does not require, before the time at which the first voltage comparator 831 determines that the absolute value of the voltage equals or exceeds the absolute value of the first threshold. The time delay may expire before or after the voltage becomes stable, i.e., the rate of change of the voltage is substantially zero. The phrase "the rate of change of the voltage is substantially zero" means that temporal change of the voltage is less than 0.1%/ns. The phrase "the rate of change of the voltage is substantially non-zero" means that temporal change of the voltage is at least 0.1%/ns.

The controller 836 may be configured to activate the second voltage comparator during (including the beginning and the expiration) the time delay. In an embodiment, the controller 836 is configured to activate the second voltage comparator at the beginning of the time delay.

The controller 836 may be configured to cause the number registered by the counter 838 to increase by one, if, during the time delay, the second voltage comparator 832 determines that the absolute value of the voltage equals or exceeds the absolute value of the second threshold. In this case, the number represents a quantity of X-ray photons reaching the detector.

In one embodiment, the controller 836 may be configured to cause the number registered by the counter 838 to increase by one, if the X-ray photon reaching the detector meets a condition, e.g. having energy within a given range or having a wavelength within a given range. The energy may be determined by measuring the voltage after stabilization of the voltage. The controller 836 may be configured to cause the voltmeter 834 to measure the voltage upon expiration of the time delay or after stabilization of the voltage.

After stabilization of the voltage or after the rate of change of the voltage becomes substantially zero, the voltage is proportional to the amount of charge carriers generated by an X-ray photon, which relates to the energy of the X-ray photon. The controller 836 may be configured to determine the energy of the X-ray photon based on voltage the voltmeter 834 measures. One way to determine the energy is by binning the voltage. The counter 838 may have a sub-counter for each bin. When the controller 836 determines that the energy of the X-ray photon falls in a bin, the controller 836 may cause the number registered in the sub-counter for that bin to increase by one. Therefore, the system 721 may be able to resolve X-ray photon energies of each X-ray photon.

The voltmeter 834 may feed the voltage it measures to the controller 836 as an analog or digital signal.

The controller 836 may be configured to connect the electrode to an electrical ground, so as to reset the voltage and discharge any charge carriers accumulated on the electrode. The controller 836 may connect the electrode to the electrical ground by controlling the reset switch 815. The switch may be a transistor such as a field-effect transistor (FET).

Figure 9:
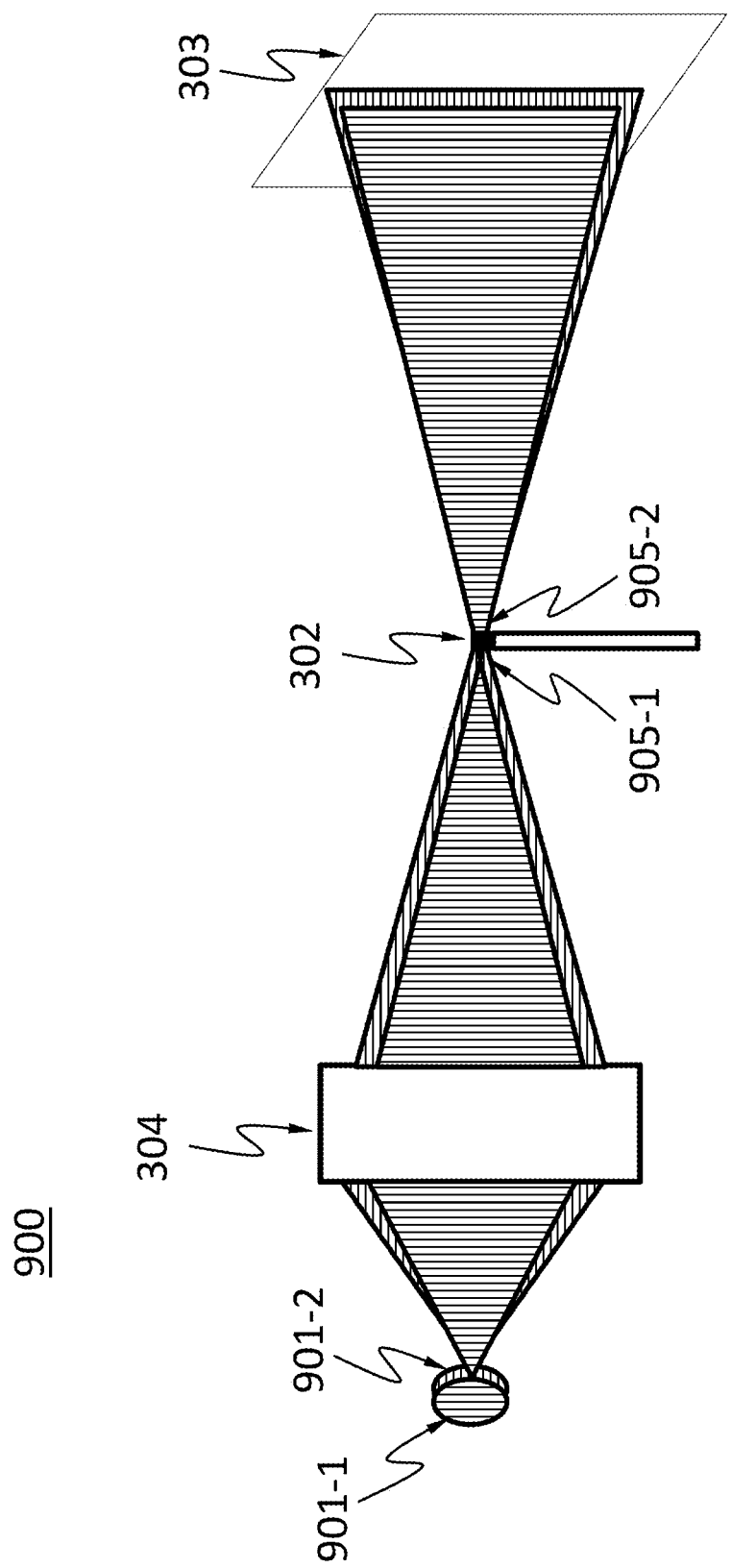
FIG. 9 schematically shows an X-ray imaging system capable of simultaneously generating two images of an object, according to an embodiment of the present teaching.

FIG. 9 schematically shows an X-ray imaging system 900 (e.g. an X-ray microscope or an X-ray CT system) capable of simultaneously generating two images of an object, according to an embodiment of the present teaching. The structure of the X-ray imaging system 900 may be similar to the structure of the X-ray microscope 300, except that the X-ray source 901 is a microfocus X-ray source that can irradiate X-rays with at least two wavelengths simultaneously, e.g. two K-alpha emission lines 901-1, 901-2 ("K-lines" hereinafter) irradiated from two types of metals.

According to an embodiment, the X-ray source 901 may be a multilayer metal source. The X-ray source 901 may include an X-ray tube with a target including multiple layers. Each layer may include a metal from e.g. Sc, Ti, V, Cr, Mn, Fe, and Cu. Each layer may be as thin as 100 nm to 10 μm. The X-ray emitted by the X-ray source 901 may include different K-lines corresponding to different metals in the multilayer metal target. The energy difference between any two of the K-lines is at least 200 eV, which is detectable by the detector disclosed herein.

According to an embodiment, the two K-lines 901-1, 901-2 have an energy difference of about 500 eV. As discussed above, the focusing optics 304 may be a Fresnel zone plate that has different focal lengths for different K-lines with different wavelengths. Therefore, after the two K-lines are condensed by the focusing optics 304, two focal points 905-1, 905-2 are formed respectively.

According to an embodiment, the sample 302 may be placed between the two focal points 905-1, 905-2 as shown in FIG. 9.

As discussed above, the detector 303 may be a semiconductor X-ray detector capable of counting photons that have energies in a predetermined range of interest. In the example of FIG. 9, the detector 303 can simultaneously generate two images of the sample 302 each of which corresponds to one of the two K-lines. For example, for each absorbed X-ray photon, the detector 303 can determine energy of the absorbed X-ray photon (e.g. by measuring a voltage of an electrode), and thus determine the absorbed X-ray photon is from which of the two K-lines. If the absorbed X-ray photon is from e.g. K-line 901-1, the detector 303 will increase the number of photons for K-line 901-1 by one. For an X-ray detector having an array of pixels, the photon counting may be performed at each pixel. For each pixel, the detector 303 can determine the number of X-ray photons that are from a K-line and collected by the pixel. For example, over a period of time, pixel i counted $n_i$ photons from K-line 901-1 and $m_i$ photons from K-line 901-2, where i=1 . . . N, and N represents the number of pixels of the detector 303. By compiling the numbers $n_i$, $m_i$, the detector 303 may generate an image of sample 302 with two colors or two K-line wavelengths. This is a simple way to enable color X-ray microscopic imaging with a very low cost.

In a similar manner, three or more K-lines can be used by the X-ray source 901 to generate a color image of the sample 302.

A detector capable of resolving photon energy, e.g. the semiconductor X-ray detector 700, may be used for phase-contrast X-ray imaging (PCI) (also known as phase-sensitive X-ray imaging). A detector capable of resolving photon energy may be less sensitive to a non-monochromic source, especially for X-ray microscopy. PCI encompasses techniques that form an image of an object at least partially using the phase shift (including the spatial distribution of the phase shift) of an X-ray beam caused by that object. One way to obtain the phase shift is transforming the phase into variations in intensity.

PCI can be combined with tomographic techniques to obtain a 3D-distribution of the real part of the refractive index of the object. PCI is more sensitive to density variations in the object than conventional intensity-based X-ray imaging (e.g., radiography). PCI is especially useful for imaging soft tissues.

FIG. 10A schematically shows a system 1110 suitable for PCI, according to an embodiment of the present teaching. In this embodiment, the system 1110 comprises the semiconductor X-ray detector 700 described herein. The semiconductor X-ray detector 700 is configured to move to and capture images of an object 1102 exposed to incident X-ray 1101 at different distances from the object 1102. The images may not necessarily be captured simultaneously. The phase may be determined from the images, for example, using algorithms based on the linearization of the Fresnel diffraction integral. As can be understood by one skilled in the art, the detector in the system 1110 may be any detector that can resolve photon energy, which may not require monochromic light source.

Figure 10B:
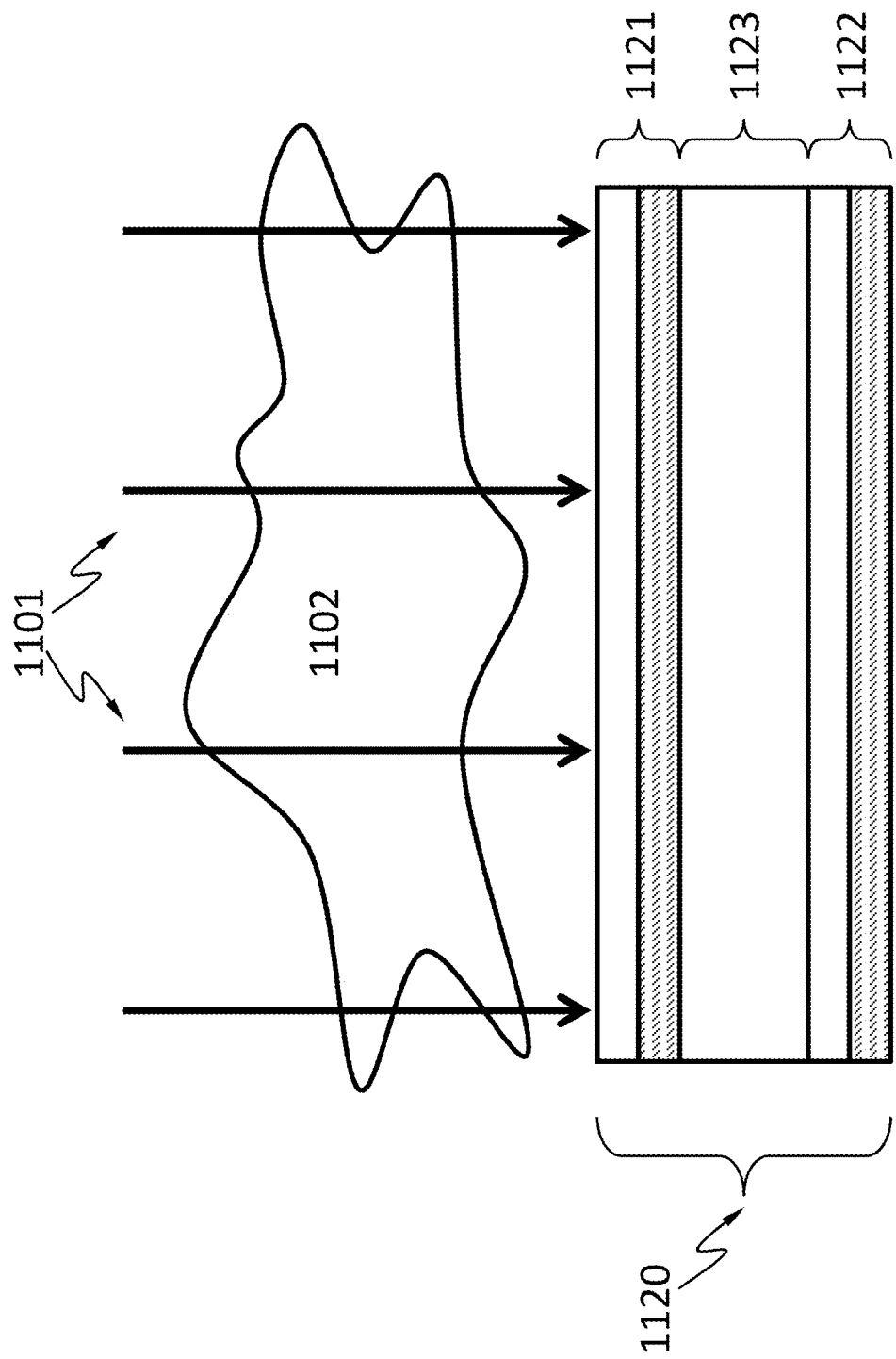
FIG. 10B schematically shows another system suitable for PCI, according to an embodiment of the present teaching.

FIG. 10B schematically shows another system 1120 suitable for PCI, according to an embodiment of the present teaching. In this embodiment, the system 1120 may include at least two X-ray detectors 1121 and 1122. One or both of the two X-ray detectors 1121, 1122 is the semiconductor X-ray detector 700 described herein. The X-ray detectors 1121 and 1122 may be spaced apart by a spacer 1123. The spacer 1123 may have very little absorption of the X-ray. For example, the spacer 1123 may have a very small mass attenuation coefficient (e.g., <10 $cm^2g^{-1}$, <1 $cm^2g^{-1}$, <0.1 $cm^2g^{-1}$, or <0.01 $cm^2g^{-1}$). The mass attenuation coefficient of the spacer 1123 may be uniform (e.g., variation between every two points in the spacer 1123 less than 5%, less than 1% or less than 0.1%). The spacer 1123 may cause the same amount of changes to the phase of X-ray passing through the spacer 1123. For example, the spacer 1123 may be a gas (e.g., air), a vacuum chamber, may comprise aluminum, beryllium, silicon, or a combination thereof. As can be understood by one skilled in the art, the detector in the system 1110 may be any detector that can resolve photon energy, which may not require monochromic light source.

The system 1120 can be used to obtain the phase shift of incident X-ray 1101 caused by an object 1102 being imaged. The X-ray detectors 1121 and 1122 can capture two images (i.e., intensity distributions) simultaneously. Because of the X-ray detectors 1121 and 1122 are separated by the spacer 1123, the two images are different distances from the object 1102. The phase may be determined from the two images, for example, using algorithms based on the linearization of the Fresnel diffraction integral.

Figure 11:
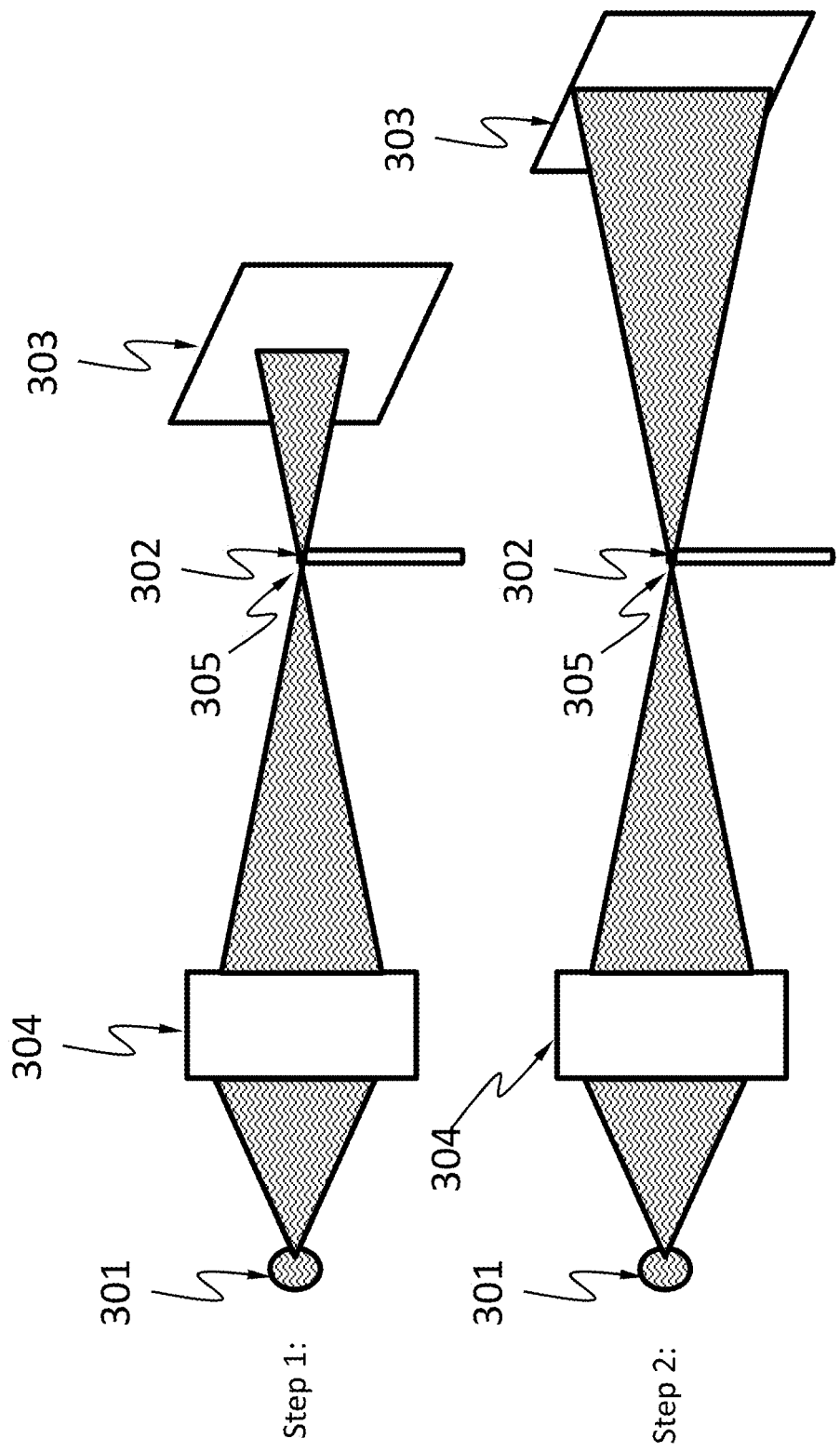
FIG. 11 illustrates a method of using the X-ray microscope in FIG. 3 for phase-contrast X-ray imaging (PCI), according to an embodiment of the present teaching.

According to an embodiment, FIG. 11 illustrates a method of using the X-ray microscope 300 in FIG. 3 for phase-contrast X-ray imaging (PCI), according to an embodiment of the present teaching. As shown in FIG. 11, the method includes two steps: Step 1 and Step 2. At Step 1, the X-ray source 301 irradiates X-ray to form a first image of the sample 302 detected by the detector 303, when the detector 303 is located at a first distance from the sample 302. At Step 2, the X-ray source 301 irradiates X-ray again to form a second image of the sample 302 detected by the detector 303, when the detector 303 is located at a second distance from the sample 302. The phase shift may be determined from the two images, for example, using algorithms based on the linearization of the Fresnel diffraction integral. When the detector 303 can resolve photon energy, the X-ray source 301 may be a non-monochromic source.

According to an embodiment, the sample 302 may be rotated for micro CT, e.g. based on a reconstruction algorithm as in cone-beam CT.

Figure 12:
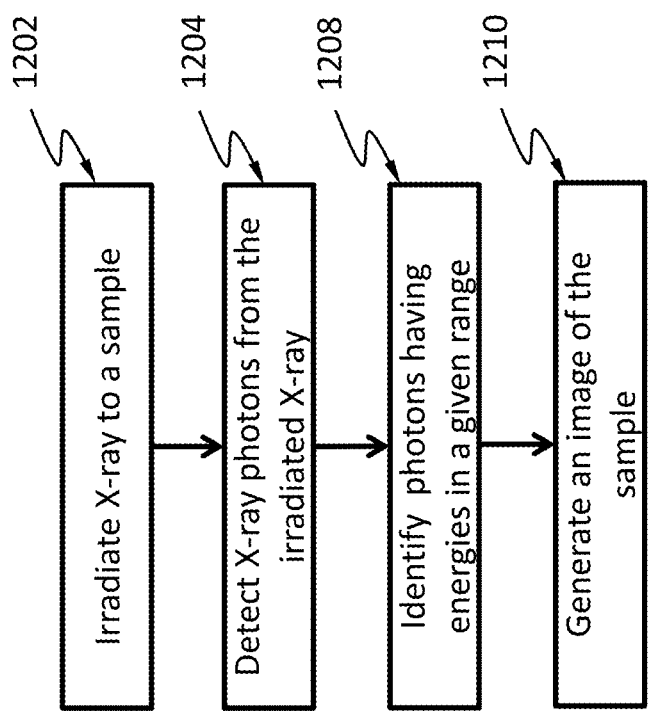
FIG. 12 shows a flow chart of a method suitable for X-ray microscopy based on a detector capable of resolving photon energy, according to an embodiment of the present teaching.

FIG. 12 shows a flow chart of a method suitable for X-ray microscopy based on a detector capable of resolving photon energy, according to an embodiment of the present teaching. At 1202, irradiate X-ray to a sample, e.g. by an X-ray source disclosed herein. At 1204, detect X-ray photons from the irradiated X-ray, e.g. by a detector disclosed herein. At 1208, X-ray photons having energies in a given range are identified, e.g. by a detector capable of resolving photon energy. The given range may be predetermined and of interest for X-ray microscopy. At 1210, generate an image of the sample, e.g. based on the identified X-ray photons that have energies in the given range of interest.

Figure 13:
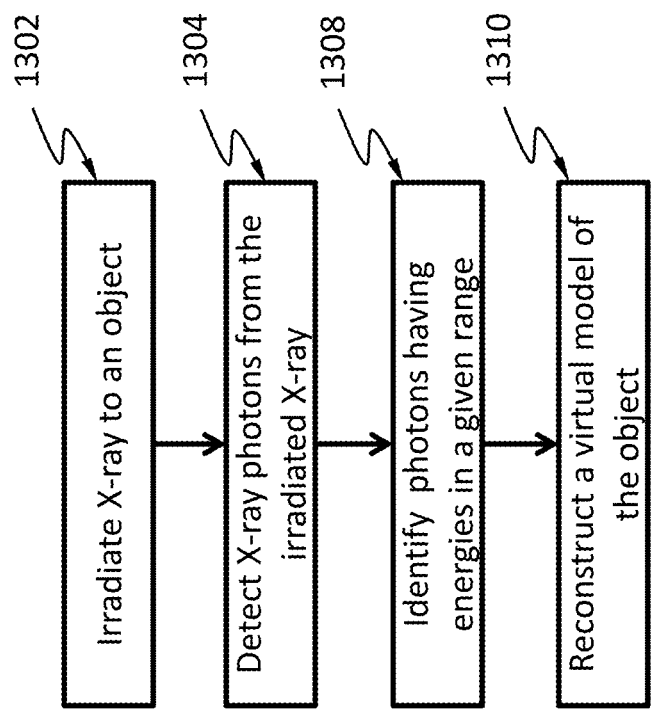
FIG. 13 shows a flow chart of a method suitable for X-ray CT based on a detector capable of resolving photon energy, according to an embodiment of the present teaching.

FIG. 13 shows a flow chart of a method suitable for X-ray CT based on a detector capable of resolving photon energy, according to an embodiment of the present teaching. At 1302, irradiate X-ray to an object, e.g. by an X-ray source disclosed herein. At 1304, detect X-ray photons from the irradiated X-ray, e.g. by a detector disclosed herein. At 1308, X-ray photons having energies in a given range are identified, e.g. by a detector capable of resolving photon energy. The given range may be predetermined and of interest for X-ray CT. An image may be formed with X-ray photons with energies within the range. At 1310, reconstruct a virtual model (e.g. a 3D model) of the object, e.g. based on the identified X-ray photons that have energies in the given range of interest. For example, the virtual model may be constructed from images obtained from multiple directions and under multiple orientations of the sample, where each of the images is formed with X-ray photons with energies within the range.

Figure 14:
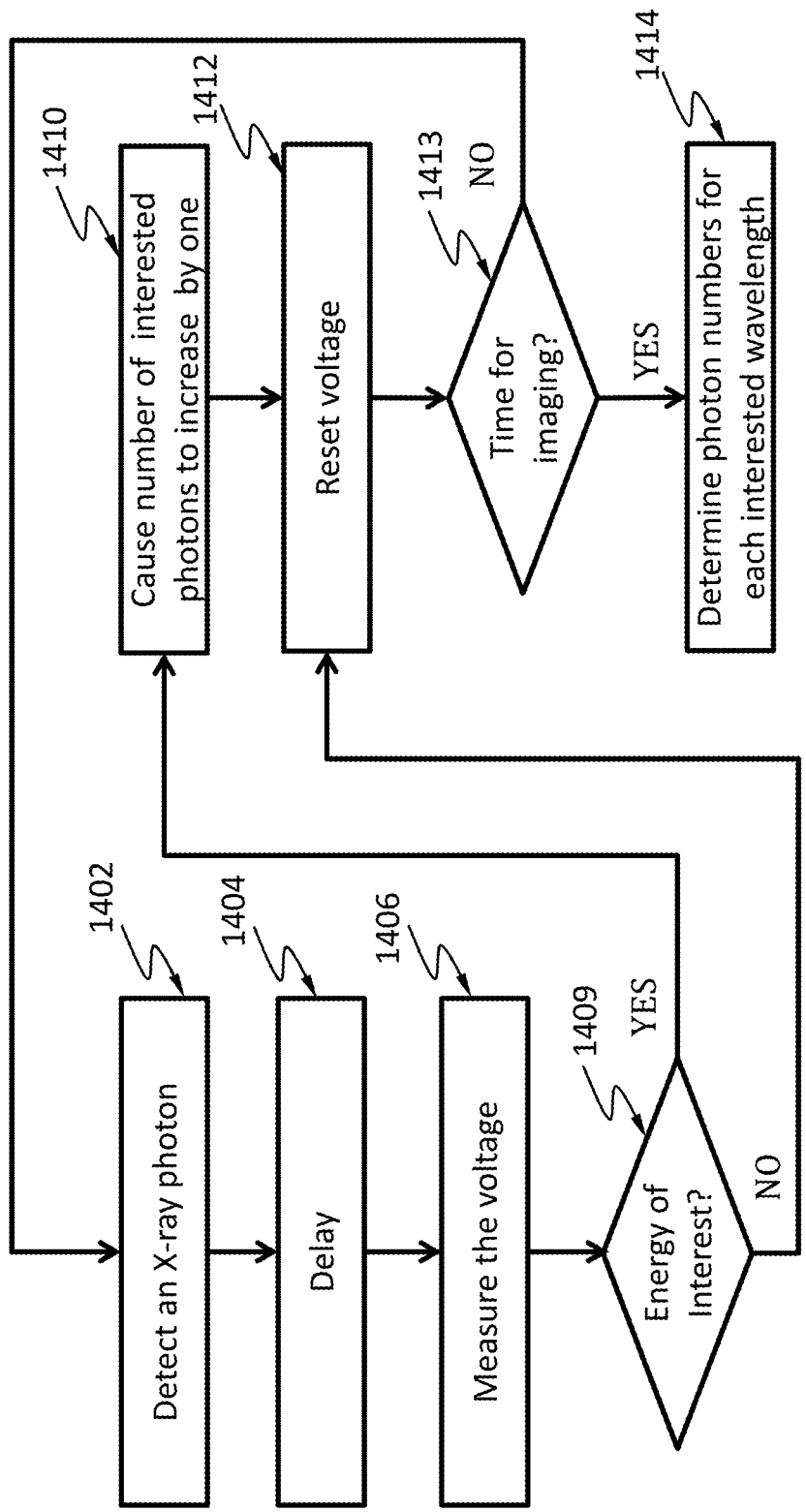
FIG. 14 shows a flow chart for a method suitable for detecting X-ray based on a system such as the electronic system 721 of Pixel 1 in FIG. 8, according to an embodiment of the present teaching.

FIG. 14 shows a flow chart for a method suitable for detecting X-ray in X-ray imaging (e.g. X-ray CT or X-ray microscopy) based on a system such as the electronic system 721 of Pixel 1 in FIG. 8, according to an embodiment of the present teaching. At 1402, detect an X-ray photon collected by Pixel 1. The detection can be based on an increase of a voltage of an electrode, e.g. when the voltage starts to increase or reaches the first threshold. The electrode may be a diode or an electrical contact of a resistor exposed to X-ray.

At 1404, delay by a predetermined period of time. The voltage is then measured at 1406.

At 1409, it is determined based on the voltage whether the X-ray photon energy is of interest to the detector, e.g. by determining whether the X-ray photon energy is within one or more predetermined ranges. For example, a predetermined range of photon energy may be 8 to 9 keV. If the X-ray photon energy is of interest to the detector, the process moves to 1410, to cause, e.g., using the controller 836, the number registered in the counter 838 to increase by one. The number here represents a quantity of X-ray photons that are collected by the pixel and have energies within a predetermined range of interest. The process then goes on to 1412. Otherwise, if the X-ray photon energy is not of interest to the detector, the process moves to 1412 directly.

At 1412, reset the voltage to an electrical ground, e.g., by connecting the electrode of the diode or an electrical contact of a resistor to an electrical ground.

At 1413, it is determined whether it is time to generate an image of the sample in the X-ray imaging system. For example, an image of the sample may be generated after a period of time, e.g. 1 second, 10 seconds, or 1 minute. If it is time for imaging, the process moves to 1414, to determine photon numbers for each interested wavelength that corresponds to a predetermined range of photon energy. Otherwise, if it is not time for imaging, the process may go back to 1402.

The process illustrated in FIG. 14 may be performed on each pixel of a detector. When it is time for imaging, the detector can compile the photon numbers for each interested X-ray wavelength from all pixels to form a single-color or multi-color image of the sample, based on a spatial distribution of the X-ray intensity.

Figure 15:
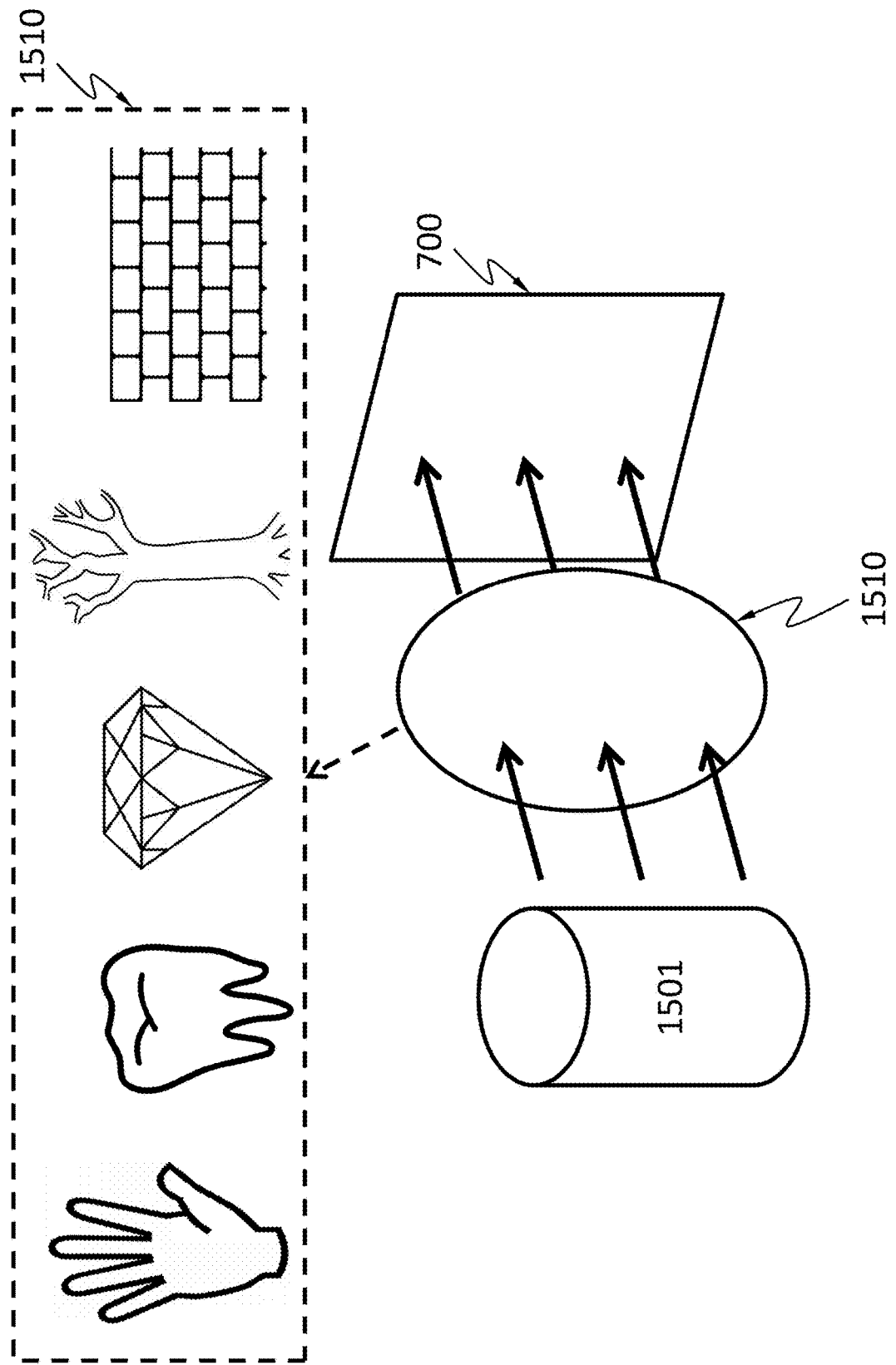
FIG. 15 schematically shows a system comprising an X-ray detector described herein, suitable for performing X-ray radiography on human mouth, human chest, human abdomen, diamond, plant, building material, etc., according to an embodiment of the present teaching.

FIG. 15 schematically shows a system comprising the semiconductor X-ray detector 700 described herein. The system comprises an X-ray source 1501. X-ray emitted from the X-ray source 1501 penetrates an object 1510 (e.g., a human body part such as chest, limb, abdomen), is attenuated by different degrees by the internal structures of the object 1510 (e.g., diamonds, trees, building material, bones, teeth, muscle, fat and organs, etc.), and is projected to the semiconductor X-ray detector 700. The semiconductor X-ray detector 700 forms an image by detecting the intensity distribution of the X-ray. The system may be used for medical imaging such as chest X-ray radiography, abdominal X-ray radiography, dental X-ray radiography, etc. The system may be used for industrial CT, such as diamond defect detection, scanning a tree to visualize year periodicity and cell structure, scanning building material like concrete after loading, etc. As can be understood by one skilled in the art, the detector in FIG. 15 may be any detector that can resolve photon energy.

Figure 16:
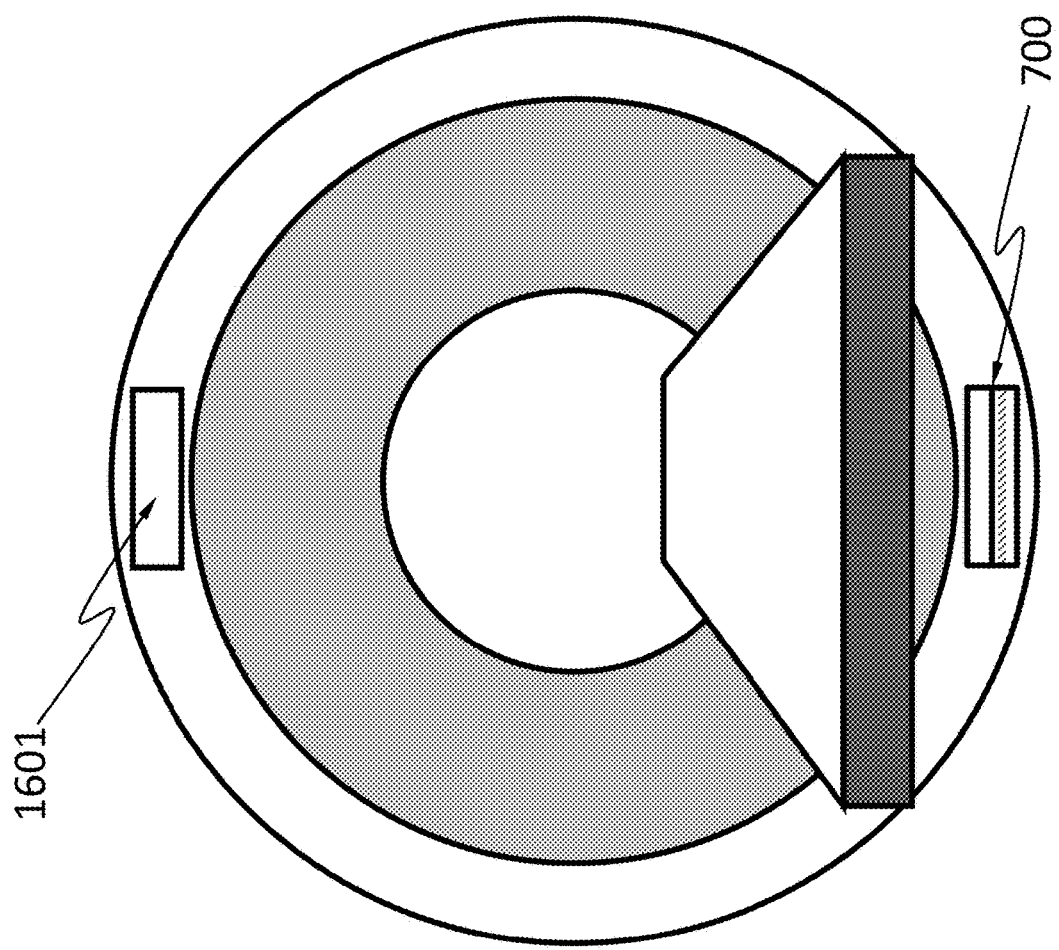
FIG. 16 schematically shows an X-ray computed tomography (X-ray CT) system comprising an X-ray detector described herein, according to an embodiment of the present teaching.

FIG. 16 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 700 described herein and an X-ray source 1601. The semiconductor X-ray detector 700 and the X-ray source 1601 may be configured to rotate synchronously along one or more circular or spiral paths. As can be understood by one skilled in the art, the detector in FIG. 16 may be any detector that can resolve photon energy.

The semiconductor X-ray detector 700 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 700 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An X-ray microscope, comprising:
an X-ray source configured emit X-ray;
focusing optics configured to focus the X-ray from the X-ray source into a focal point where a sample is placed; and
a detector configured to:
detect X-ray photons from the sample,
determine energy of the detected X-ray photons, and
generate an image of the sample based on the detected X-ray photons that have energies in a predetermined range;
wherein the detector comprises:
an X-ray absorption layer comprising an electrode;
a first voltage comparator configured to compare a voltage of the electrode to a first threshold;
a second voltage comparator configured to compare the voltage to a second threshold;
a counter configured to register a number of X-ray photons absorbed by the X-ray absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, when the second voltage comparator determines that an absolute value of the voltage equals or exceeds an absolute value of the second threshold.

2. The X-ray microscope of claim 1, wherein the X-ray photons from the sample comprise X-ray photons having energies in the predetermined range and X-ray photons having energies outside the predetermined range.

3. The X-ray microscope of claim 1, wherein the focusing optics are further configured to focus the X-ray from the X-ray source into a virtual point source before the sample.

4. The X-ray microscope of claim 1, wherein the detector is further configured to determine a number of the detected X-ray photons that have energies in the predetermined range.

5. The X-ray microscope of claim 1, wherein:
the detector comprises an array of pixels; and
the detector is further configured to determine a number of the detected X-ray photons that have energies in the predetermined range, for each of the pixels.

6. The X-ray microscope of claim 1, wherein the detector is further configured to:

determine a first number of X-ray photons that are detected by the detector and have energies in a first range; and determine a second number of X-ray photons that are detected by the detector and have energies in a second range.

7. The X-ray microscope of claim 6, wherein the detector is further configured to generate a first image of the sample based on the first number of X-ray photons and a second image of the sample based on the second number of X-ray photons.

8. A method, comprising:

focusing X-ray into a focal point where a sample is placed;

detecting a first plurality of X-ray photons from the sample using a detector, at a first distance from the sample;

determining energy of the first plurality of X-ray photons; and generating a first image of the sample based on the first plurality of X-ray photons that have energies in a predetermined range;

wherein the detector comprises:

an X-ray absorption layer comprising an electrode;

a first voltage comparator configured to compare a voltage of the electrode to a first threshold;

a second voltage comparator configured to compare the voltage to a second threshold;

a counter configured to register a number of X-ray photons absorbed by the X-ray absorption layer;

a controller;

wherein the controller is configured to start a time delay from a time at which the first voltage comparator determines that an absolute value of the voltage equals or exceeds an absolute value of the first threshold;

wherein the controller is configured to activate the second voltage comparator during the time delay;

wherein the controller is configured to cause the number registered by the counter to increase by one, when the second voltage comparator determines that an absolute value of the voltage equals or exceeds an absolute value of the second threshold.

9. The method of claim 8, wherein the first plurality of X-ray photons from the sample comprise X-ray photons having energies in the predetermined range and X-ray photons having energies outside the predetermined range.

10. The method of claim 8, further comprising focusing the X-ray into a virtual X-ray point source before the sample.

11. The method of claim 8, wherein generating the first image is performed by a detector comprising a plurality of pixels and generating the image further comprises:

determining a number of the first plurality of X-ray photons that have energies in the predetermined range, for each of the pixels; and generating the image of the sample based on the number.

12. The method of claim 8, further comprising:

determining a first number of X-ray photons that are detected and have energies in a first range; and determining a second number of X-ray photons that are detected and have energies in a second range.

13. The method of claim 12, further comprising generating a first image of the sample based on the first number of X-ray photons and a second image of the sample based on the second number of X-ray photons.

14. The method of claim 8, further comprising:

detecting a second plurality of X-ray photons from the sample, at a second distance from the sample, the second distance being different from the first distance;

determining energy of the second plurality of X-ray photons; and generating a second image of the sample based on the second plurality of X-ray photons that have energies in a predetermined range.

* * * * *